United States Patent [19]

Chen

[11] Patent Number: 6,117,176
[45] Date of Patent: Sep. 12, 2000

[54] ELASTIC-CRYSTAL GEL

[75] Inventor: John Y. Chen, Pacifica, Calif.

[73] Assignee: Applied Elastomerics, Inc., South San Francisco, Calif.

[21] Appl. No.: 08/863,794

[22] Filed: May 27, 1997

Related U.S. Application Data

[63] Continuation-in-part of application No. 08/819,675, Mar. 17, 1997, Pat. No. 5,884,639, and a continuation-in-part of application No. 08/719,817, Sep. 30, 1996, and a continuation-in-part of application No. 08/665,343, Jun. 17, 1996, and a continuation-in-part of application No. 08/612,586, Mar. 8, 1996, which is a continuation-in-part of application No. PCT/US94/04278, Apr. 19, 1994, and a continuation-in-part of application No. PCT/US94/07314, Jun. 27, 1994, and a continuation-in-part of application No. 08/288,690, Aug. 11, 1994, Pat. No. 5,633,286, and a continuation-in-part of application No. 08/581,188, Dec. 29, 1995, and a continuation-in-part of application No. 08/581,191, Dec. 29, 1995, Pat. No. 5,760,117, and a continuation-in-part of application No. 08/581,125, Dec. 29, 1995, said application No. 08/288,690, said application No. PCT/US94/07314, said application No. 08/152,734, Nov. 15, 1993, Pat. No. 5,624,294.

[51] Int. Cl.[7] ................. A61F 2/78; A61F 2/80; C08J 5/02; C08J 51/00

[52] U.S. Cl. ............. 623/36; 428/319.3; 428/319.7; 428/319.9; 428/378; 428/441; 428/462; 428/521; 428/537.1; 524/270; 524/474; 524/476; 524/490; 524/505; 623/8; 623/11; 623/18; 623/20; 623/33; 623/37

[58] Field of Search .................. 524/270, 474, 524/476, 490, 505; 428/319.3, 319.7, 319.9, 328, 441, 462, 521, 537.1, 688; 623/11, 36, 37, 8, 18, 20, 33

[56] References Cited

U.S. PATENT DOCUMENTS

| | | | |
|---|---|---|---|
| 3,660,849 | 5/1972 | Jonnes | 2/2.1 |
| 3,821,149 | 6/1974 | Makowski | 260/30.6 |
| 3,827,999 | 8/1974 | Crossland | 260/33.6 |
| 3,860,013 | 1/1975 | Czapor | 132/91 |
| 4,136,699 | 1/1979 | Collins | 128/290 |
| 4,151,057 | 4/1979 | St. Clair . | |
| 4,176,240 | 11/1979 | Sabia | 174/23 |
| 4,259,540 | 3/1981 | Sabia . | |
| 4,351,913 | 9/1982 | Patel . | |
| 4,361,508 | 11/1982 | Bourland | 523/173 |
| 4,369,284 | 1/1983 | Chen . | |
| 4,432,607 | 2/1984 | Levy | 350/96.34 |
| 4,492,428 | 1/1985 | Levy . | |
| 4,497,538 | 2/1985 | Patel . | |
| 4,509,821 | 4/1985 | Stenger | 350/96.23 |
| 4,600,261 | 7/1986 | Debbaut . | |
| 4,610,738 | 9/1986 | Jervis | 156/49 |
| 4,618,213 | 10/1986 | Chen . | |
| 4,643,924 | 2/1987 | Uken | 428/35 |
| 4,662,692 | 5/1987 | Uken | 339/96 |
| 4,678,664 | 7/1987 | Schmolka | 424/65 |
| 4,680,233 | 7/1987 | Camin | 428/424.6 |
| 4,690,831 | 9/1987 | Uken | 427/44 |
| 4,692,369 | 9/1987 | Nomi | 428/198 |
| 4,709,982 | 12/1987 | Corne | 427/44 |
| 4,716,183 | 12/1987 | Gamarra | 522/90 |
| 4,721,832 | 1/1988 | Toy | 174/87 |
| 4,764,535 | 8/1988 | Leicht . | |
| 4,798,853 | 1/1989 | Handlin | 523/173 |
| 4,801,346 | 1/1989 | Huddleston . | |
| 4,822,834 | 4/1989 | Blevins | 524/427 |
| 4,833,193 | 5/1989 | Sieverding . | |
| 4,842,931 | 6/1989 | Zook | 428/354 |
| 4,864,725 | 9/1989 | Debbaut | 29/871 |
| 4,865,905 | 9/1989 | Uken | 428/220 |
| 4,880,676 | 11/1989 | Pulgcerver | 428/35.7 |
| 4,880,878 | 11/1989 | Himes | 525/89 |
| 4,883,431 | 11/1989 | Uken . | |
| 4,888,070 | 12/1989 | Clark . | |
| 4,889,171 | 12/1989 | Covington | 428/304 |
| 4,889,403 | 12/1989 | Zucker . | |
| 4,900,877 | 2/1990 | Dubrow | 174/35 |
| 4,909,756 | 3/1990 | Jervis . | |
| 4,929,211 | 5/1990 | Resnick | 446/14 |
| 4,942,270 | 7/1990 | Gamarra | 174/93 |
| 4,944,363 | 7/1990 | Osher | 273/58 |
| 4,944,973 | 7/1990 | Follette . | |
| 4,968,747 | 11/1990 | Mallikarjun | 525/74 |
| 4,983,008 | 1/1991 | Campbell | 350/96.16 |
| 5,026,054 | 6/1991 | Osher | 273/58 |

(List continued on next page.)

FOREIGN PATENT DOCUMENTS

| | | |
|---|---|---|
| 1268431 | 1/1969 | United Kingdom . |
| PCT/WO 88/00603 | 1/1988 | WIPO . |
| PCT/WO 90/05166 | 5/1990 | WIPO . |
| PCT/WO 91/05014 | 4/1991 | WIPO . |
| PCT/WO 93/05113 | 3/1993 | WIPO . |
| PCT/WO 93/23472 | 11/1993 | WIPO . |

OTHER PUBLICATIONS

"Styrene–Diene Triblock Copolymers: Orientation Conditions and Mechanical Properties of the Oriented Materials" A. Weill and R. Pixa, Journal of Polymer Science Polymer Symposium 58, 381–394 (1977).

Septon Trade Literature, Kuraray Co., Ltd. 1995.8 (4,000) and 15 pages.

Shell Chemical Co., Data Sheets: EKP–207 (093094–02) and L–1203 (SC:2384–950.

(List continued on next page.)

*Primary Examiner*—Herbert J. Lilling

[57] ABSTRACT

Novel crystal gels and articles are formed from one or more block copolymers having at least one crystalline midblock and high levels of a plasticizer, said midblock segment having an amount of crystallinity sufficient to achieve improvements in one or more physical properties including improved crack propagation resistance, improved tear resistance, improved resistance to fatigue and resistance to catastrophic failure not obtainable in amorphous gels.

10 Claims, 11 Drawing Sheets

U.S. PATENT DOCUMENTS

| | | | |
|---|---|---|---|
| 5,059,748 | 10/1991 | Allen | 174/87 |
| 5,068,138 | 11/1991 | Mitchell | 428/36.8 |
| 5,085,597 | 2/1992 | Story | 439/521 |
| 5,088,734 | 2/1992 | Glava | 273/73 |
| 5,098,421 | 3/1992 | Zook | 604/367 |
| 5,126,182 | 6/1992 | Douglas | 428/90 |
| 5,149,736 | 9/1992 | Gamarra | 524/490 |
| 5,153,254 | 10/1992 | Chen | 524/505 |
| 5,159,022 | 10/1992 | Ikematu | 525/250 |
| 5,167,649 | 12/1992 | Zook | 604/307 |
| 5,173,573 | 12/1992 | Jervis | 174/138 |
| 5,177,143 | 1/1993 | Toy | 524/848 |
| 5,181,914 | 1/1993 | Zook | 604/307 |
| 5,191,752 | 3/1993 | Murphy | 54/44.5 |
| 5,221,534 | 6/1993 | Deslauriers | 424/78.03 |
| 5,239,723 | 8/1993 | Chen | 15/104 |
| 5,262,468 | 11/1993 | Chen | 524/476 |
| 5,313,019 | 5/1994 | Brusselmans | 174/93 |
| 5,324,222 | 6/1994 | Chen | 446/34 |
| 5,330,452 | 7/1994 | Zook | 604/307 |
| 5,334,646 | 8/1994 | Chen | 524/474 |
| 5,336,708 | 8/1994 | Chen | 524/474 |
| 5,407,445 | 4/1895 | Tautvydas et al. | 623/8 |
| 5,459,193 | 10/1995 | Anderson | 524/505 |
| 5,475,890 | 12/1995 | Chen | 15/104 |
| 5,479,952 | 1/1996 | Zachariades | 132/321 |
| 5,508,334 | 4/1996 | Chen | 524/476 |
| 5,559,165 | 9/1996 | Paul | 523/111 |
| 5,606,149 | 2/1997 | Yaworski | 174/92 |
| 5,618,882 | 4/1997 | Hammond | 525/92 |
| 5,624,294 | 4/1997 | Chen | 446/253 |
| 5,626,657 | 5/1997 | Pearce | 106/122 |
| 5,633,286 | 5/1997 | Chen | 524/474 |
| 5,655,947 | 8/1997 | Chen | 446/46 |
| 5,760,117 | 6/1998 | Chen | 524/476 |
| 5,830,237 | 11/1998 | Kania | 623/36 |
| 5,884,639 | 3/1999 | Chen | 428/521 |
| 5,888,216 | 3/1999 | Haberman | 636/36 |

OTHER PUBLICATIONS

SC:1102–89 Shell Chemical Technical Bulletin"KRATON® Thermoplastic Rubber in the Oil Gels", Apr. 1989.

Septon, High Performance Thermoplastic Rubber, Kurraray Co., LTD., 1995.

Kraton Polymers, May 1997, Shell Chemical Company.

Melt Miscibility In Blends Of Polypropylene, Polystryenhe–Block–Poly(Ethylene–Sat–Butyle-ne)–Block–Polystyrene, and Processing Oil From Melting Point Depression, Ohlesson et al., Polymer Engineering and Science, 1996, vol. 36, No. 11.

Blends And Thermoplastic Interpenetrating Polymer Networks Of Polypropytlene And Polystyrene–Block–Poly-(Ethylene–Stat–Butylene)–Block–Polytstyrene Triblock Copolymer. 1: Morphology And Structure–Related Properties, Ohlesson, et al., Polymer Engineering and Science, Feb. 1996, vol. 36, No. 4.

Migration And Blooming Of Waxes To The Surface Of Rubber Vulcanizates, Nah, et al., J. Of Polymer Science: Polymer Physics Ed., vol. 18, 511–521 (1980).

| | |
|---|---|
| M1 | Fabric or Cloth |
| G | Gel |
| GM | Gel-Sponge or Gel-Foam |
| M2 | Foam or Sponge |
| M3 | Synthetic Resin or Plastic |
| M4 | Fibre |
| M5 | Concrete |
| M6 | Metal or Metal Sponge |
| M7 | Wood |
| M8 | Wire or Screening |
| M9 | Refractory Material |
| M10 | Other Material |

S - EP - E - EP - S

ELASTIC-CRYSTAL GEL

RELATED APPLICATIONS

This application is a continuation-in-part of the following applications: U.S. Ser. No: 08/819,675 filed Mar. 17, 1997 now U.S. Pat. No. 5,884,639; U.S. Ser. No: 08/719,817 filed Sep. 30, 1996, U.S. Ser. No: 08/665,343 filed Jun. 17, 1996 which is a Continuation-in-part of U.S. Ser. No: 08/612,586 filed Mar. 8, 1996 which is a Continuation-in-part of Ser. Nos: PCT/US94/04278 filed Apr. 19, 1994 (published May 26, 1995 No. WO95/13851); PCT/US94/07314 filed Jun. 27, 1994 (published Jan. 4, 1996 No. WO 96/00118); 08/288, 690 filed Aug. 11, 1994; now U.S. Pat. No. 5,633,286 08/581,188 filed Dec. 29, 1995; 08/581,191 filed Dec. 29, 1995; now U.S. Pat. No. 5,760,117 Ser. No. 08/581,125 filed Dec. 29, 1995. In turn U.S. Ser. Nos. 08/581,188 now abandoned; 08/581,191; and 08/581,125 are continuation-in-parts of the following applications: Ser. Nos.: 08/288,690, filed Aug. 11, 1994, PCT/US94/07314 filed Jun. 27, 1994 (CIP of PCT/US94/04278, filed Apr. 19, 1994 which in turn is a CIP of 07/957,290); now U.S. Pat. No. 5,334,646 Ser. No. 08/152,734, filed Nov. 15, 1993 now U.S. Pat. No. 5,629,294 (CIPs of 114.688; 935,540; 876,118; 705,096; 957,290; 705,711).

FIELD OF THE INVENTION

The present invention is directed to novel block copolymer gels.

BACKGROUND OF THE INVENTION

The EB copolymer midblock of conventional SEBS is almost totally amorphous and the EP midblock of SEPS is amorphous and non-crystalline.

Gels made from such block copolymers are rubbery and exhibit substantially no hysteresis. Their rubbery-ness and lack of hysteresis are due to the amorphous nature of their midblocks. Such gels are hereafter referred to as "non-crystalline gels" or more simply as "amorphous gels".

In general, the overall physical properties of amorphous gels are better at higher gel rigidities. The amorphous gels, however, can fail catastrophically when cut or notched while under applied forces of high dynamic and static deformations, such as extreme compression, torsion, high tension, high elongation, and the like. Additionally, the development of cracks or crazes resulting from a large number of deformation cycles can induce catastrophic fatigue failure of amorphous gel composites, such as tears and rips between the surfaces of the amorphous gel and substrates or at the interfaces of interlocking material(s) and gel. Consequently, such amorphous gels are inadequate for the most demanding applications involving endurance at high stress and strain levels over an extended period of time.

SUMMARY OF THE INVENTION

I have now discovered gels with novel properties which comprises: (I) 100 parts by weight of one or more high viscosity linear, branched, star-shaped (radial), or multiarm block copolymers or mixtures of two or more such block copolymers, said block copolymers having one or more midblocks, said midblocks comprising one or more substantially crystalline polyethylene midblocks and with nil, one or more amorphous midblocks; optionally in combination with a selected amount of one or more of a (II) polymer or copolymer, and selected amounts of a plasticizing oil (III) sufficient to achieve gel rigidities of from less than about 2 gram Bloom to about 1,800 gram Bloom with the proviso that said block copolymers having nil amorphous midblocks are combined with at least one block copolymer having at least one amorphous midblock.

As used herein, the term "gel rigidity" in gram Bloom is determined by the gram weight required to depress a gel a distance of 4 mm with a piston having a cross-sectional area of 1 square centimeter at 23° C.

The gels comprising thermoplastic elastomer block copolymers having one or more substantially crystalline polyethylene midblocks of the invention are hereafter referred to as "elastic-crystalline gels" or simpler "crystal gels". The block midblocks of copolymers forming the crystal gels of the invention are characterized by sufficient crystallinity as to exhibit a melting endotherm of at least about 40° C. as determined by DSC curve.

The various types of high viscosity block copolymers employed in forming the crystal gels of the invention are of the general configurations A-Z-A and (A-Z)$_n$, wherein the subscript n is two or more. In the case of multiarm block copolymers where n is 2, the block copolymer denoted by (A-Z)$_n$ is A-Z-A. It is understood that the coupling agent is ignored for sake of simplicity in the description of the (A-Z)$_n$ block copolymers.

The end block segment (A) comprises a glassy amorphous polymer end block segment which can be polystyrene, poly(alpha-methylstyrene), poly(o-methylstyrene), poly(m-methylstryene), poly(p-methylstyrene) and the like, preferably, polystyrene. The midblocks (Z) comprises one or more midblocks of substantially crystalline poly(ethylene) (simply denoted by "-E- or (E)") with or without one or more amorphous midblocks of poly(butylene), poly (ethylene-butylene), poly(ethylene-propylene) or combination thereof (the amorphous midblocks are denoted by "-B- or (B)", "-EB- or (EB)", and "-EP- or (EP)" respectively or simply denoted by "-W- or (W)" when referring to one or more of the amorphous midblocks as a group) The A and Z portions are incompatible and form a two or more-phase system consisting of sub-micron amorphous glassy domains (A) interconnected by (Z) chains. The glassy domains serve to crosslink and reinforce the structure. This physical elastomeric network structure is reversible, and heating the polymer above the softening point of the glassy domains temporarily disrupt the structure, which can be restored by lowering the temperature.

The (I) linear block copolymers are characterized as having a Brookfield Viscosity value at 5 weight percent solids solution in toluene at 30° C. of from less than about 40 cps to about 60 cps and higher, advantageously from about 40 cps to about 160 cps and higher, more advantageously from about 50 cps to about 180 cps and higher, still more advantageously from about 70 cps to about 210 cps and higher, and even more advantageously from about 90 cps to about 380 cps and higher.

The (I) branched, star-shaped (radial), or multiarm block copolymers are characterized as having a Brookfield Viscosity value at 5 weight percent solids solution in toluene at 30° C. of from about 80 cps to about 380 cps and higher, advantageously from about 150 cps to about 260 cps and higher, more advantageously from about 200 cps to about 580 cps and higher, and still more advantageously from about 100 cps to about 800 cps and higher.

The crystal gels can be made in combination with a selected amount of one or more selected polymers and copolymers (II) including thermoplastic crystalline polyurethane elastomers with hydrocarbon blocks, homopolymers, copolymers, block copolymers, polyethylene copolymers, polypropylene copolymers, and the like described below.

The crystal gels of the invention are also suitable in physically interlocking or forming with other selected materials to form composites combinations. The materials are selected from the group consisting of paper, foam, plastic, fabric, metal, metal foil, concrete, wood, glass, various natural and synthetic fibers, including glass fibers, ceramics, synthetic resin, and refractory materials.

The various aspects and advantages will become apparent to those skilled in the art upon consideration of the accompanying disclosure.

DESCRIPTION OF THE DRAWINGS

FIG. 1. Representative components materials of composites forming useful articles of the invention.

DESCRIPTION OF THE INVENTION

Figure 2A:
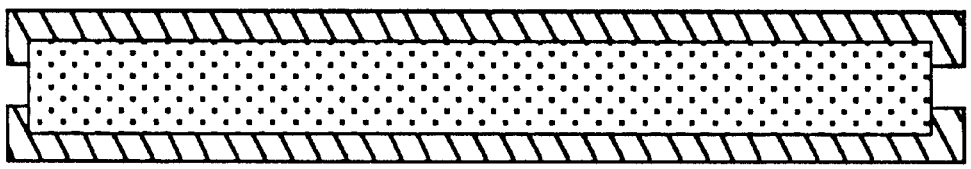
FIG. 2. Representative sectional view of composite articles of the invention (FIG. 2a.=MGM, FIG. 2b.=GMG, FIG. 2c.=MGMGMGM, FIG. 2d.=foam entirely interlocked with composition).
Figure 2B:
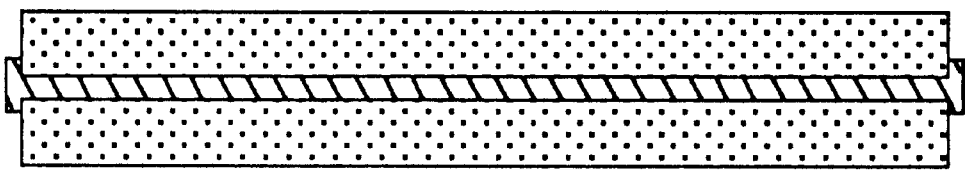
Figure 2C:
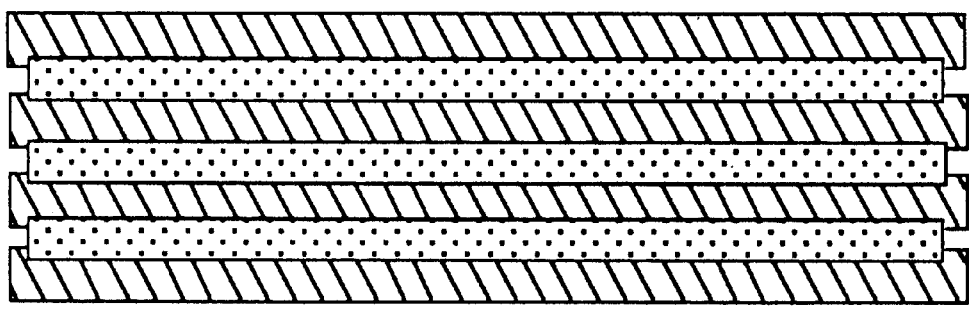
Figure 2D:

Thermoplastic elastomer SEBS gels are described in my earlier applications and patents: U.S. Ser. Nos: 581,188 filed Dec. 29, 1995; 581,191 filed Dec. 29, 1995; 581,125 filed Dec. 29, 1995; PCT/US94/04278 filed Apr. 19, 1994; PCT/US94/07314 filed Jun. 27, 1994; 08/288,690 filed Aug. 11, 1994; 152,734, filed Nov. 15, 1993; 152,735, 11/15/93; 114.688, filed Aug. 30, 1993; 935,540 filed Aug. 24, 1992; 876,118 filed Apr. 29, 1992; 705,096 filed May 23, 1991; 527,058 filed May 21, 1990; 921,752 filed Oct. 21, 1986; 458,703, filed Jan. 17, 1983; 916,731, filed Jun. 19, 1978; 815,315, filed Jul. 13, 1977; 778,343, filed Mar. 17, 1977; U.S. Pat. Nos. 5,262,468; 5,153,254; 4,618,213; and 4,369,284. Various patents on thermoplastic elastomers are described in U.S. Pat. Nos. 3,595,942, Reissue 27,145-28, 236; 3,772,234; 4,116,917; and 4,687,815. Other non-patent publications related to S-EB-S polymers include: W. P. Gergen, "Uniqueness of Hydrogenated Block Copolymers for Elastomeric Applications," presented at the German Rubber Meeting, Wiesbaden, 1983; Kautsch, Gummi, Kunstst. 37, 284 (1984). W. P. Gergen, et al., "Hydrogenated Block Copolymers," Paper No. 57, presented at a meeting of the Rubber Division ACS, Los Angeles, Apr. 25, 1985. Encyclopedia of Polymer Science and Engineering, Vol. 2, pp 324–434, "Block Copolymers". L. Zotteri and et al., "Effect of hydrogenation on the elastic properties of poly (styrene-b-diene-b-styrene) copolymers", Polymer, 1978, Vol. 19, April. J. Kenneth Craver, et al., Applied Polymer Science, Ch. 29, "Chemistry and Technology of Block Polymers", pp. 394–429, 1975. Y. Mahajer and et al., "The influence of Molecular Geometry on the Mechanical Properties of homopolymers and Block Polymers of Hydrogenated Butadiene and Isoprene" reported under U.S. ARO Grant No. DAAG29-78-G-0201. J. E. McGrath, et al., "Linear and Star Branched Butadiene-Isoprene Block Copolymers and Their Hydrogenated Derivatives", Chem. Dept, Virginia Polytechnic Institute and State University Blacksturg, Va., reported work supported by Army Research Office. Legge, Norman R., "Thermoplastic Elastomers", Charles Goodyear Medal address given at the 131st Meeting of the Rubber Division, American Chemical Society, Montreal, Quebec, Canada, Vol. 60, G79-G115, May 26–29, 1987. Falk, John Carl, and et al., "Synthesis and Properties of Ethylene-Butylene-1 Block Copolymers", Macromolecules, Vol. 4, No. 2, pp. 152–154, March-April 1971. Morton, Maurice, and et al., "Elastomeric Polydiene ABA Triblock Copolymers within Crystalline End Blocks", University of Arkon, work supported by Grant No. DMR78-09024 from the National Science Foundation and Shell Development Co. Yee, A. F., and et al., "Modification of PS by S-EB-S Block Copolymers: Effect of Block Length", General Electric Corporate Research & Development, Schenectady, N.Y. 12301. Siegfried, D. L., and et al., "Thermoplastic Interpenetrating Polymer Networks of a Triblock Copolymer elastomer and an Ionomeric Plastic Mechanical Behavior", Polymer Engineering and Science, January 1981, Vol. 21, No.1, pp 39–46. Clair, D. J., "S-EB-S Copolymers Exhibit Improved Wax Compatibility", Adhesives Age, November, 1988. Shell Chemical Technical Bulletin SC:1102-89, "Kraton® Thermoplastic Rubbers in oil gels", April 1989. The above applications, patents and publications are specifically incorporated herein by reference.

Legge's paper teaches the development of (conventional substantially amorphous elastomer midsegment) SEBS triblock copolymers. In the polymerization of butadiene by alkylithium initiators, 1,4-addition or 1,2-addition polymers, mixtures, can be obtained. In forming styrene butadiene triblock copolymers involving the addition of solvating agents such as ethers just before the final styrene charge is added, any excess of ethers can alter the polybutadiene structure from a 1,4-cis or trans structure to a 1,2- or 3,4-addition polymer. Using difunctional coupling agent would give linear block copolymers and multifuntional agents would give star-shaped or radial block copolymers. Hydrogenation of the 1,4-polybutadiene structure yields polyethylene, while that of the 1,2-polybutadiene yields polybutylene. The resulting polyethylene will be essentially identical with linear, high-density polyethylene with a melting point, Tm, of about 136° C. Hydrogenation of 1,2-polybutadiene would yield atactic poly(1-butene) (polybutylene). The Tg of polybutylene is around −18° C. Random mixtures of ethylene and butylene units in the chain would suppress crystallinity arising from polyethylene sequences. The objective for a good elastomer should be to obtain a saturated olefin elastomeric segment with the lowest possible Tg and the best elastomeric properties. Such an elastomer favored using styrene as the hard-block monomer and selecting the best monomer for hydrogenation of the elastomer midsegment. Using a mixture of 1,4- and 1,2- polybutadiene as the base polymer for the midsegment would result in an ethylene/butylene midsegment in the final product. The elements of selection of the midsegment composition is elastomer crystallinity and the elastomer Tg of an ethylene/butylene copolymer. Very low levels of crystallinity can be achieved around 40–50% butylene concentration. The minimum in dynamic hysteresis around 35% butylene concentration in the elastomeric copolymer. A value of 40% butylene concentration in the ethylene/butylene midsegment was chosen for the S-EB-S block copolymers.

Clair's paper teaches that the EB midblock of conventional S-EB-S polymers is a random copolymer of ethylene and 1-butene exhibiting nearly no crystallinity in the midblock. In the preparation of ethylene-butylene (EB) copolymers, the relative proportions of ethylene and butylene in the EB copolymer chain can be controlled over a broad range from almost all ethylene to almost all butylene. When the EB copolymer is nearly all ethylene, the methylene sequences will crystallize exhibiting properties similar to low density polyethylene. In differential scanning calorimeter (DCS) curves, the melting endotherm is seen on heating and a sharp crystallization exotherm is seen on cooling. As the amount of butylene in the EB copolymer is increased, the methylene sequences are interrupted by the ethyl side chains which shorten the methylene sequences length so as to reduce the amount of crystallinity in the EB copolymer. In conventional S-EB-S polymers, the amount of 1-butene is controlled at a high enough level to make the EB copolymer midblock almost totally amorphous so as to make the copolymer rubbery and soluble in hydrocarbon solvents. Clair suggests that an S-EB-S polymer retaining at least some crystallinity in the EB copolymer midblock may be desirable. Therefore, a new family of S-EB-S polymers are developed (U.S. Pat. No. 3,772,234) in which the midblock contains a higher percentage of ethylene. The molecular weights of the new crystalline midblock segment S-EB-S polymers can vary from low molecular weight, intermediate molecular, to high molecular weight; these are designated Shell GR-3, GR-1, and GR-2 respectively. Unexpectly, the highest molecular weight polymer, GR-2 exhibits an anomalously low softening point. A broad melting endotherm is seen in the DSC curves or these polymers. The maximum in this broad endotherm occurs at about 40° C.

Block copolymers with polyethylene midblocks alone do not form suitable gels for purpose of the invention. Crystalline midblock regions needs to be balanced with amorphous midblock regions in order to obtain soft, flexible and elastic gels with the desired crystalline properties that are not found in totally amorphous gels.

Figure 5:
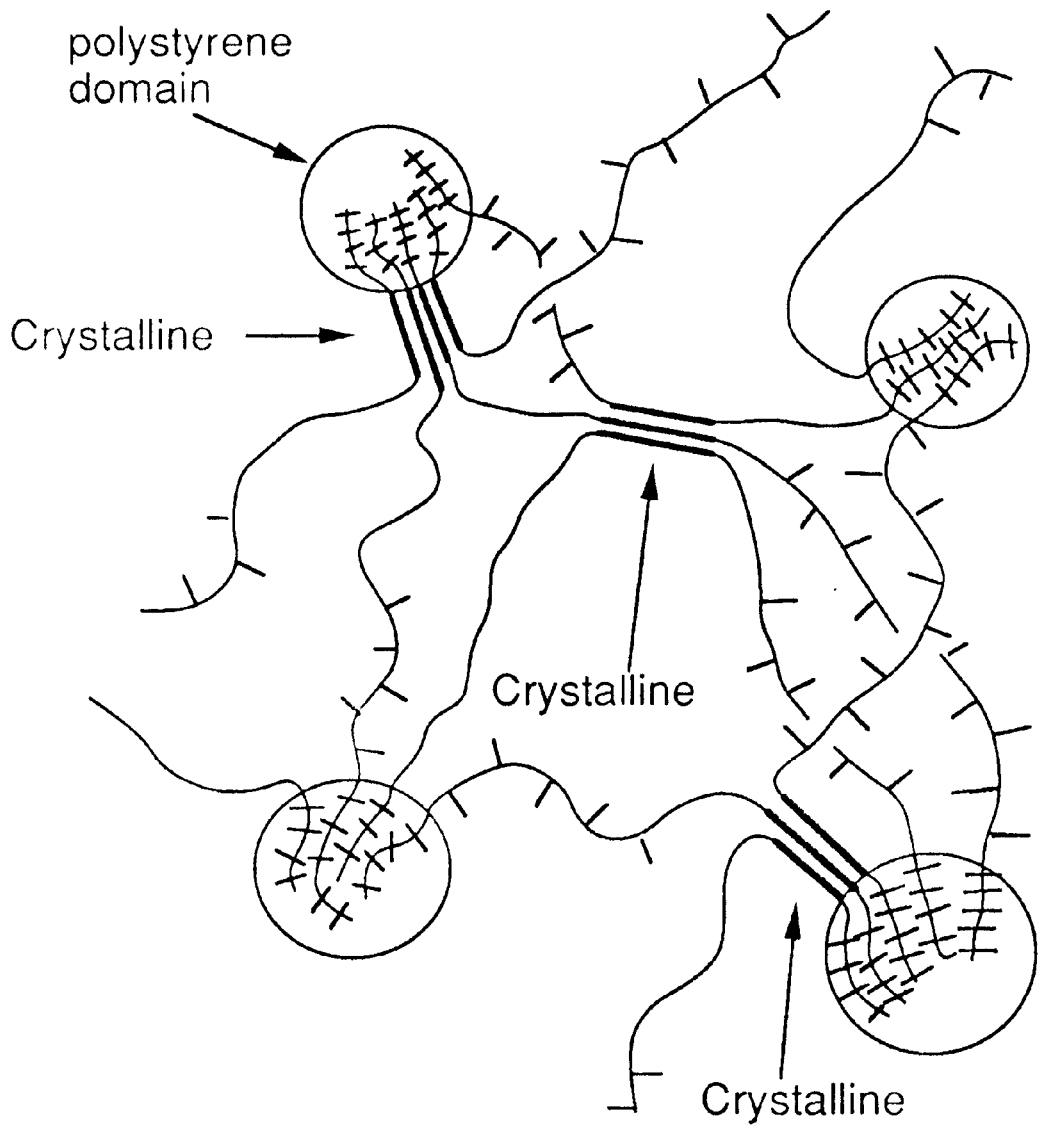
FIG. 5. Representation of S-E-EB-S crystalline/polystyrene domain/amorphous structure.
Figure 6:
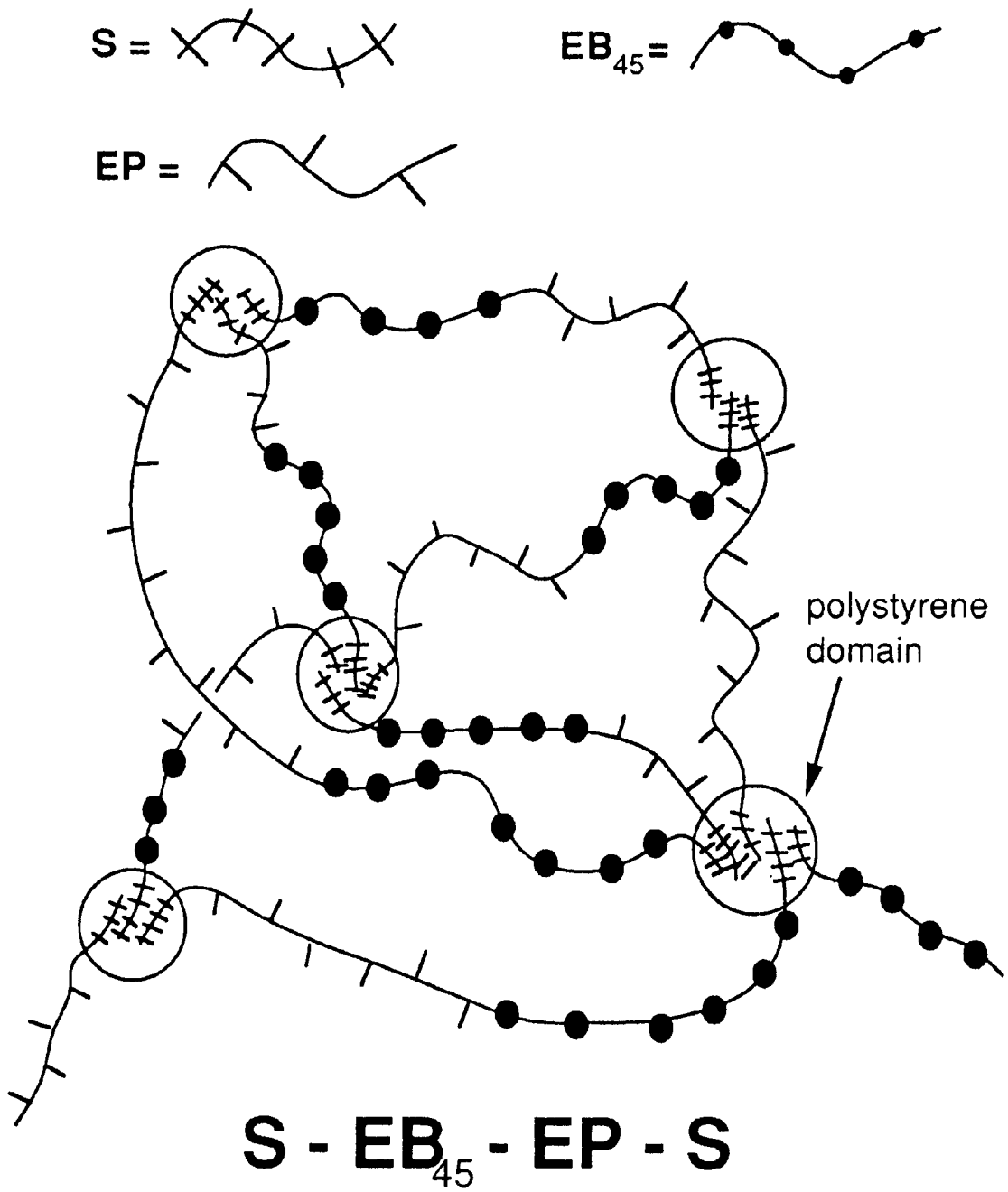
FIG. 6. Representation of S-EB$_{45}$-EP-S polystyrene domain/amorphous structure.
Figure 7:
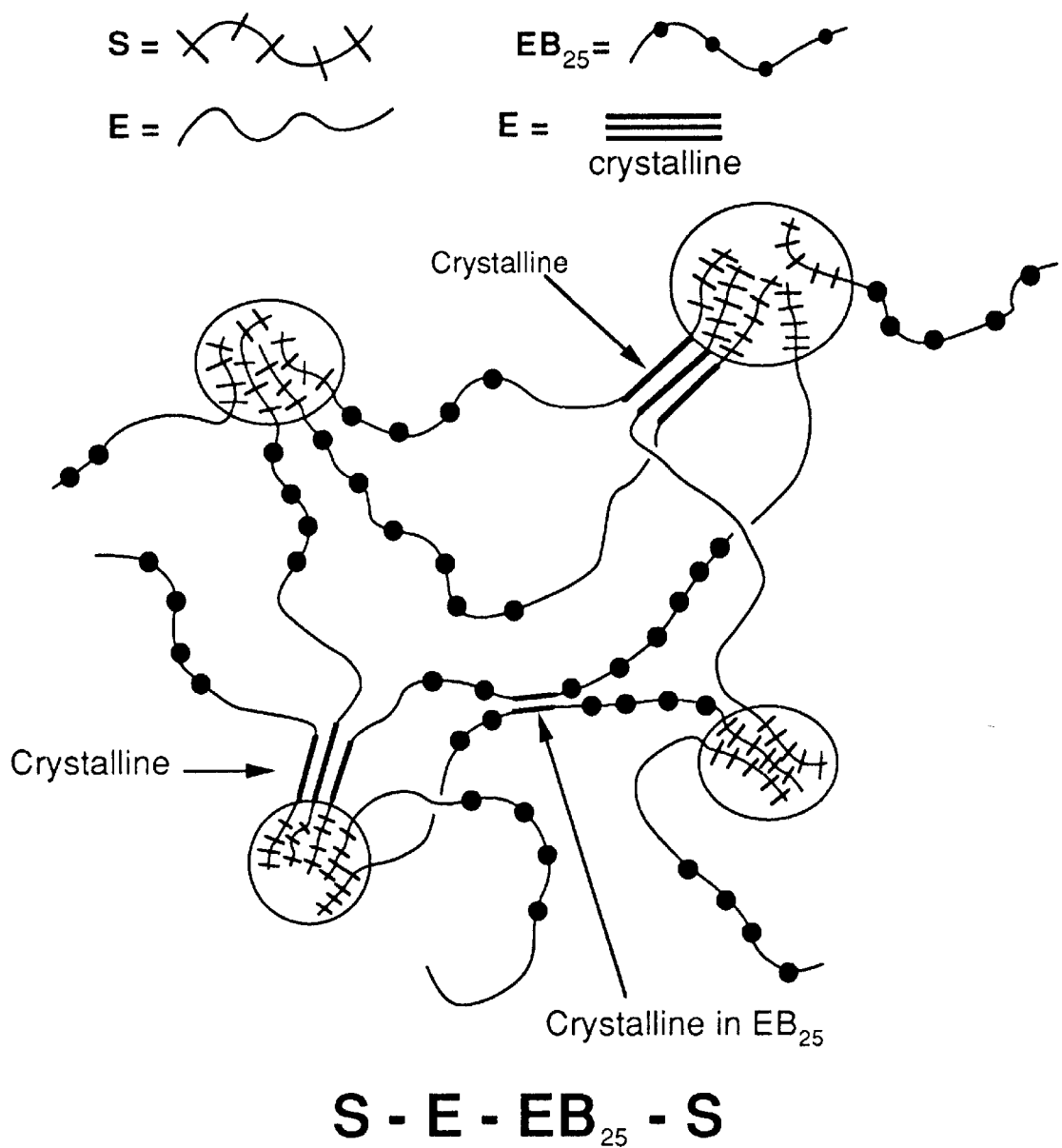
FIG. 7. Representation of S-E-EB$_{25}$-S crystalline/polystyrene domain/amorphous structure.
Figure 8:
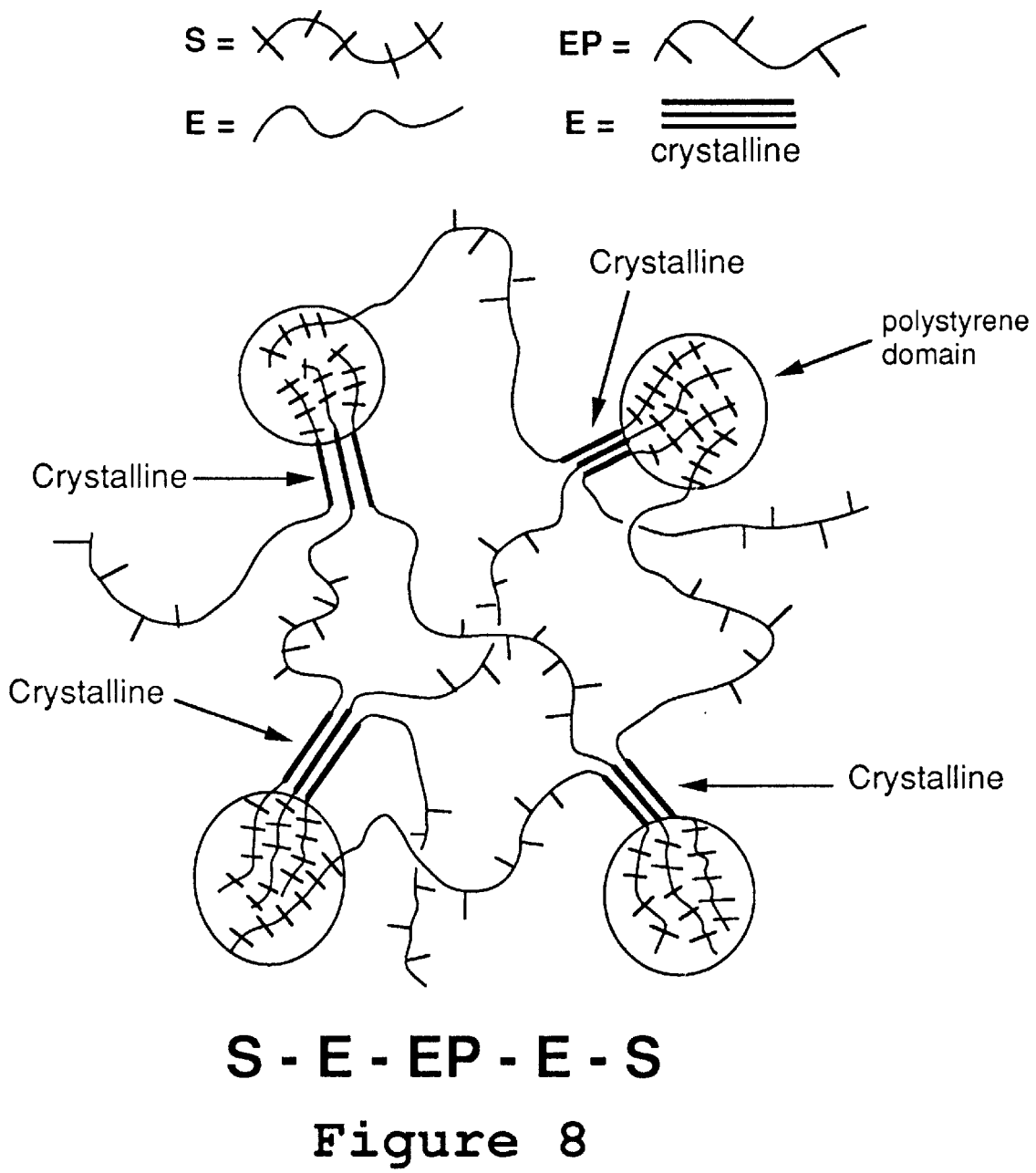
FIG. 8. Representation of S-E-EP-E-S crystalline/polystyrene domain/amorphous structure.
Figure 9:
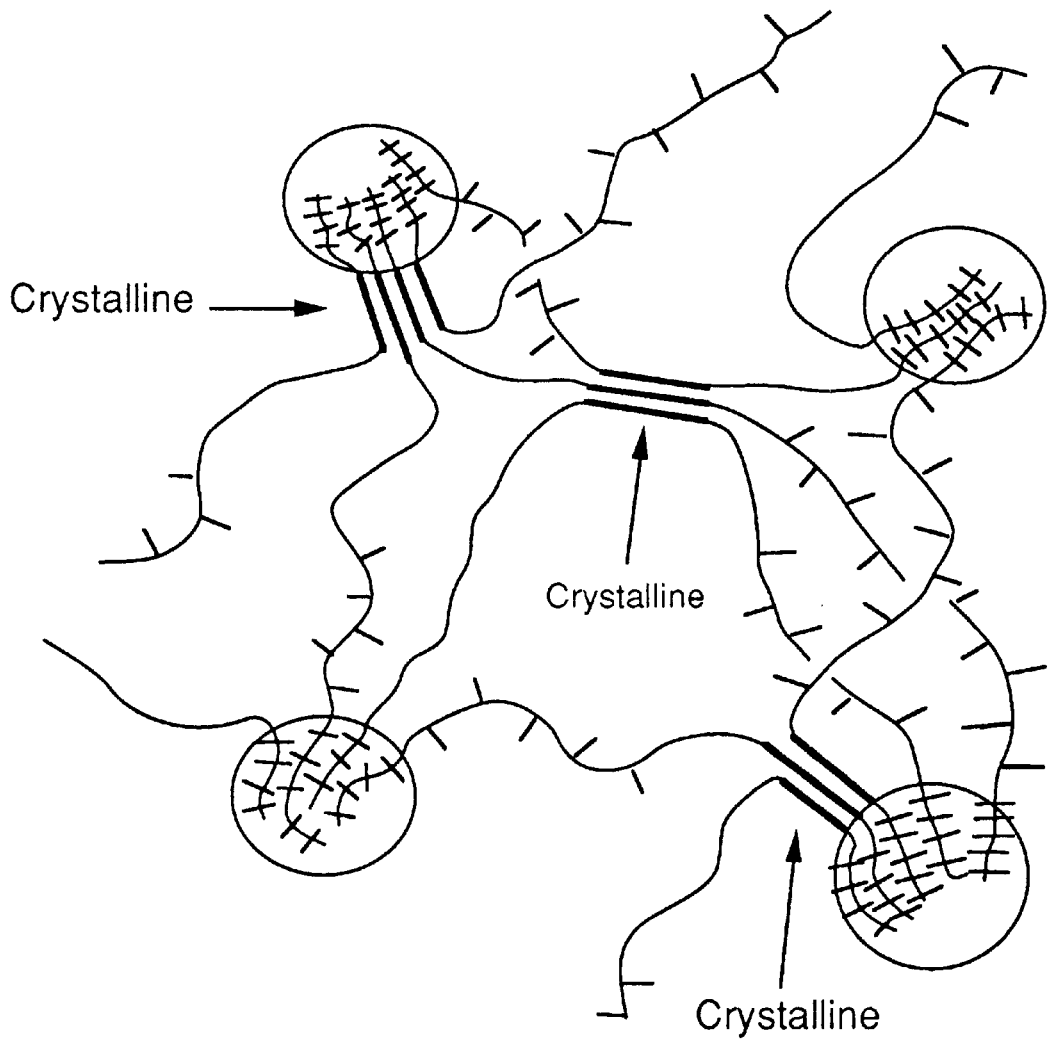
FIG. 9. Representation of S-EP-E-S crystalline/polystyrene domain/amorphous structure.
Figure 10:
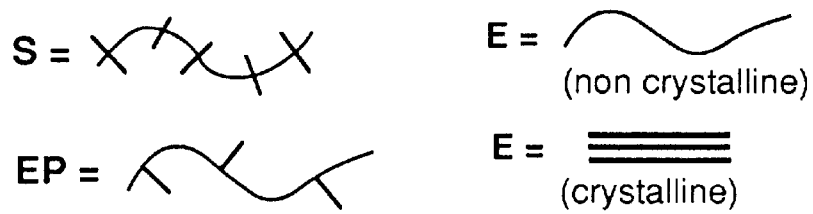
FIG. 10. Representation of S-EP-E-EP-S crystalline/polystyrene domain/amorphous structure.
Figure 10:
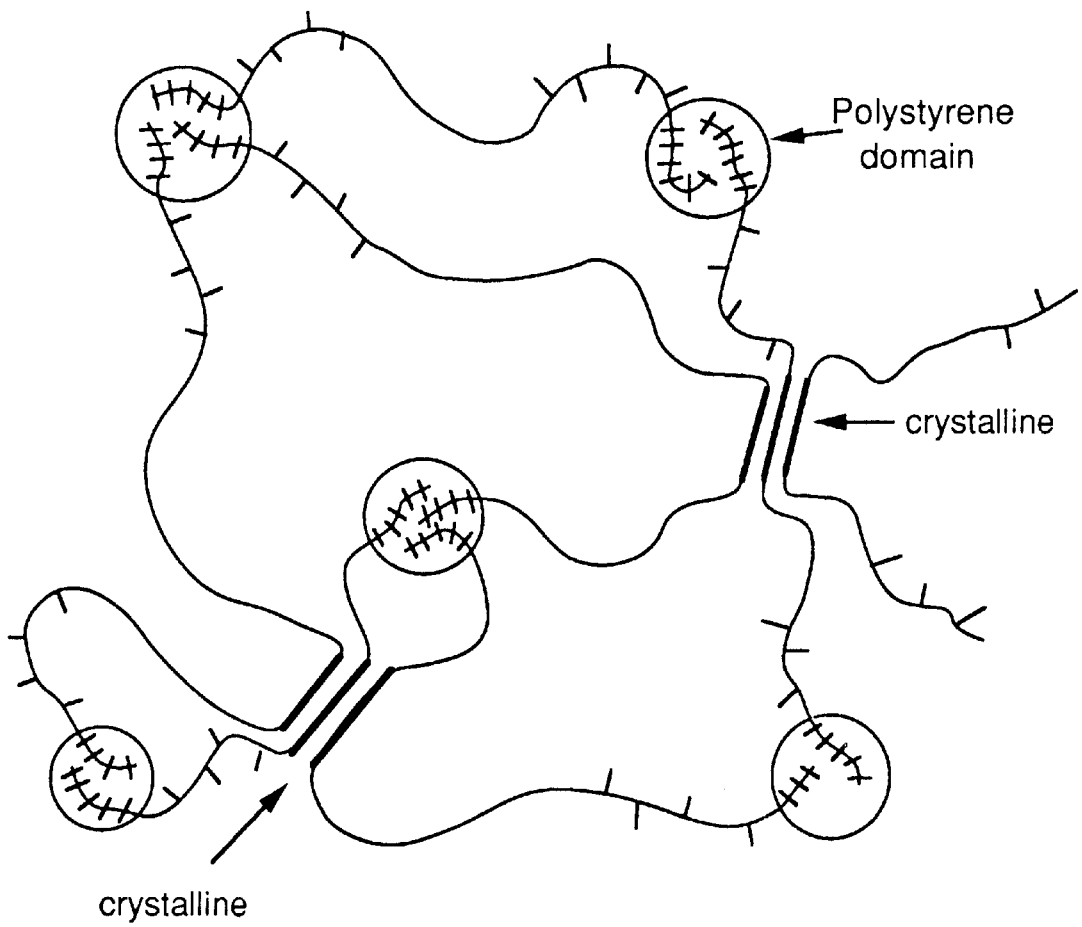
Figure 11:
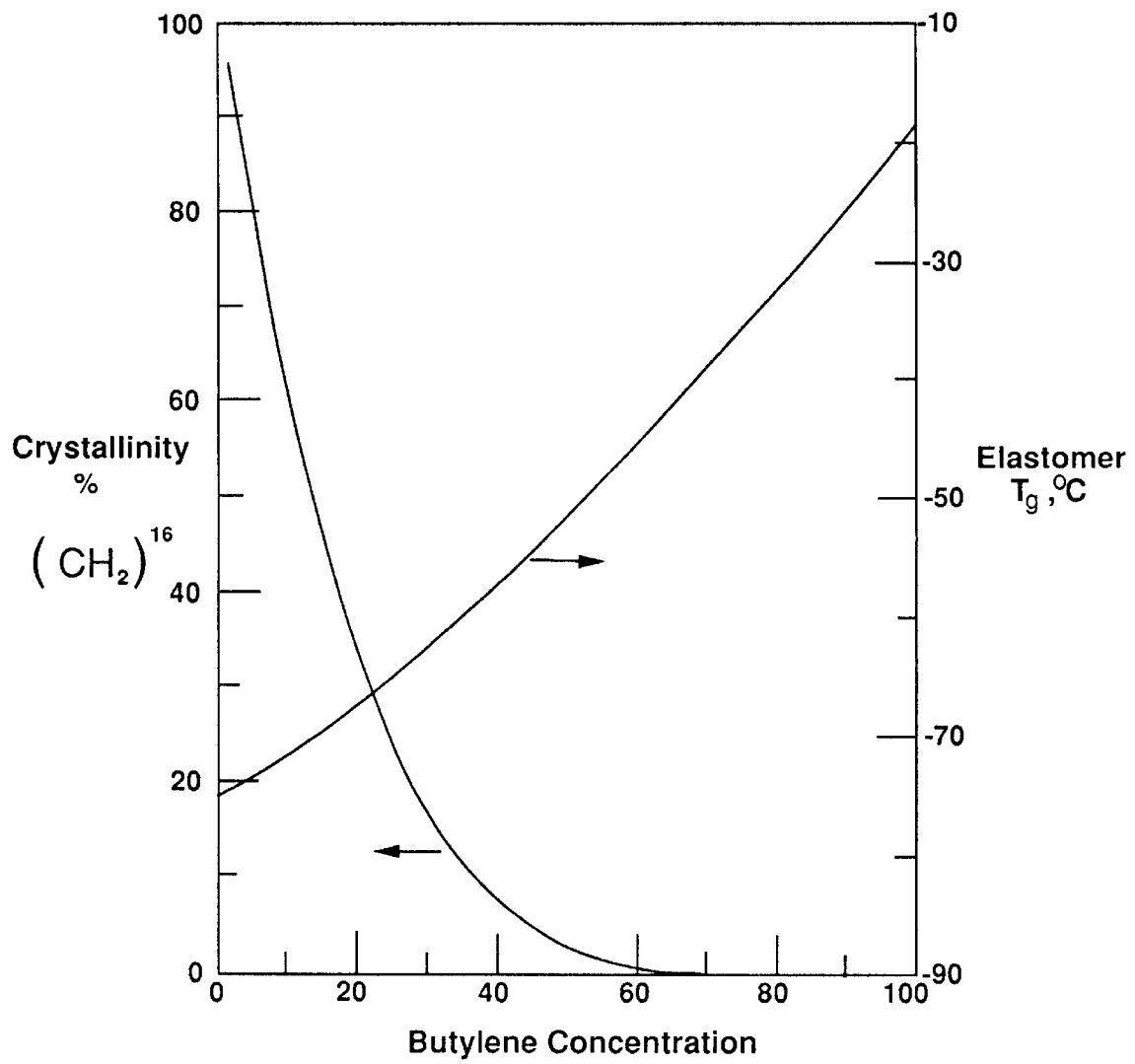
FIG. 11. Effect of butylene concentration of the percent (%) crystallinity of $(CH_2)^{16}$ units in the elastomer (midblock) phase. Reference W. P. Gergen paper at Rubber Division ACS 1985 and Legge, Norman R., paper at ACS 1987.

The various representative crystalline/glassy domain/amorphous structures of S-E-EB-S, S-EB$_{45}$-EP-S, S-E-EB$_{25}$-S, S-E-EP-E-S, S-EP-E-S and S-EP-E-EP-S are illustrate in FIGS. 5–10 above. Although the structure are spheroid representation, cylinders and plates are also within the scope of the present invention. Cylinder and plate structure are obtained with increasing glassy A end blocks. From about 15–30% by weight of A blocks, the block copolymer structure is spheroid. From about 33 about 40% by weight of A blocks, the block copolymer structure becomes cylindrical; and above about 45% A blocks, the structure becomes less cylindrical and more plate like.

In order to obtain elastic crystal gels of the invention, it is necessary that the selective synthesis of butadiene produce sufficient amounts of 1,4 poly(butadiene) that on hydrogenation can exhibit "crystallinity" in the midblocks. In order for the block copolymers forming the crystal gels of the invention to exhibit crystallinity, the crystalline midblock segments must contain long runs of —CH$_2$— groups. There should be approximately at least 16 units of —(CH$_2$)— in sequence for crystallinity. Only the (—CH$_2$—)$_4$ units can crystallize, and then only if there are at least 4 units of (—CH$_2$—)$_4$ in sequence; alternatively, the polyethylene units are denoted by [(CH$_2$—CH$_2$—CH$_2$—CH$_2$)—]$_4$, [(—CH$_2$—)$_4$]$^4$ or (—CH$_2$—)$^{16}$. The amount of (—CH2—)$^{16}$ units forming the (E) midblocks of the block copolymers comprising the crystal gels of the invention should be at least about 20% which amount is capable of exhibiting a melting endotherm in differential scanning calorimeter (DCS) curves.

Advantageously, the elastomer midblock segment should have a crystallinity of at least about 20% of (—CH$_2$—)16 units of the total mole % forming the midblocks of the block copolymer, more advantageously at least about 25%, still more advantageously at least about 30%, especially advantageously at least about 40% and especially more advantageously at least about 50% and higher. Broadly, the crystallinity of the midblocks should range from at least about 20% to about 60%, less broadly from at least about 18% to about 65%, and still less broadly from at least 22% to about 70%.

The melting endotherm in DSC curves of the crystalline block copolymers comprising at least 20% crystallinity are much higher than conventional amorphous block copolymers. The maximum in the endotherm curves of the crystalline block copolymers occurs at about 40° C., but can range from greater than about 25° C. to about 60° C. and higher. The crystalline block copolymers forming the crystal gels of the invention can exhibit melting endotherms (as shown by DSC) of about 25° C. to about 75° C. and higher. More specific melting endotherm values of the crystalline midblock block copolymers include: about 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 90° C, 100° C., 110° C., 120° C., and higher, whereas, the melting endotherm (DSC) for conventional amorphous midblock segment block copolymers are about 10° C. and lower.

The melting endotherm is seen on heating and a sharp crystallization exotherm is seen on cooling. Such midblock crystallization endothermic and exothermic characteristics are missing from DCS curves of amorphous gels. The crystallization exotherm and fusion endortherm of the crystalline block copolymer gels of the invention are determined by ASTM D 3417 method.

Generally, the method of obtaining long runs of crystalline —(CH$_2$)— is by sequential block copolymer synthesis followed by hydrogenation. The attainment of crystal gels of the instant invention is solely due to the selective polymerization of the butadiene monomer (forming the midblocks) resulting in one or more predetermined amount of 1,4 poly(butadine) blocks followed by sequential polymerization of additional midblocks and hydrogenation to produce one or more crystalline midblocks of the final block copolymers.

The crystalline block copolymers are made by sequential block copolymer synthesis, the percentage of crystallinity or (—CH$_2$—)$^{16}$ units should be at least about $(0.67)^4$ or about 20% and actual crystallinity of about 12%. For example, a selectively synthesized S-EB$_n$-S copolymer having a ratio of 33:67 of 1,2 and 1,4 poly(butadiene) on hydrogenation will result in a midblock with a crystallinity of $(0.67)^4$ or 20%. For sake of simplicity, when n is a subscript of -EB-, n denotes the percentage of $(-CH_2-)_4$ units, eg, n=33 or 20% crystallinity which is the percentage of $(0.67)^4$ or "$(-CH_2-)_{16}$" units. Thus, when n=28 or 72% of $(-CH_2-)_4$ units, the % crystallinity is $(0.72)^4$ or 26.87% crystallinity attributed to $(-CH_2-)_{16}$ units, denoted by $-EB_{28}-$. As a matter of convention, and for purposes of this specification involving hydrogenated polybutadiene: the notation -E- denotes at least about 85% of $(-CH_2-)_4$ units. The notation -B- denotes at least about 70% of $[-CH_2-CH(C_2H_5)-]$ units. The notation -EB- denotes between about 15 and 70% $[-CH_2-CH(C_2H_5)-]$ units. The notation $-EB_n-$ denotes n% $[-CH_2-CH(C_2H_5)-]$ units. For hydrogenated polyisoprene: The notation -EP- denotes about at least 90% $[-CH_2-CH(CH_3)-CH_2-CH_2-]$ units.

Generally, one or more (E) midblocks can be incorporated at various positions along the midblocks of the block copolymers. Using the sequential process for block copolymer synthesis, The (E) midblocks can be positioned as follows:

i) A-E-W-A
ii) A-E-W-E-A
ii) A-W-E-W-A
iii) A-E-W-E-W-E-W-E-A
iv) A-W-E-W-A-E-A-E-W-E-A
v) and etc.

The lower flexibility of block copolymer crystal gels due to (E) midblocks can be balanced by the addition of sequentially (W) midblocks. For example, the sequentially synthesized block copolymer S-E-EB-S can maintain a high degree of flexibility due to the presence of amorphous -EB- block. The sequential block copolymer S-E-EB-B-S can maintain a high degree of flexibility due to the presence of amorphous -EB- and -B- midblocks. The sequential block copolymer S-E-EP-E-S can maintain a high degree of flexibility due to the presence of -EP- midblock. The sequential block copolymer S-E-B-S can maintain a high degree of flexibility due to the presence of the -B- midblock. For S-E-S, where the midblock is substantially crystalline and flexibility low, physical blending with amorphous block copolymers such as S-EB-S, S-B-S, S-EP-S, S-EB-EP-S, $(S-EP)_n$ and the like can produce more softer, less rigid, and more flexible crystal gel.

Because of the (E) midblocks, the crystal gels of the invention exhibit different physical characteristics and improvements over substantially amorphous gels including damage tolerance, improved crack propagation resistance, improved tear resistance producing knotty tears as opposed to smooth tears, crystalline melting point of at least 28° C., improved resistance to fatigue, higher hysteresis, etc. Moreover, the crystal gels when stretched exhibit additional yielding as shown by necking caused by stress induced crystallinity. Additionally, the crystallization rates of the crystalline midblocks can be controlled and slowed depending on thermal history producing time delay recovery upon deformation.

Regarding resistance to fatigue, fatigue (as used herein) is the decay of mechanical properties after repeated application of stress and strain. Fatigue tests give information about the ability of a material to resist the development of cracks or crazes resulting from a large number of deformation cycles. Fatigue test can be conducted by subjecting samples of amorphous and crystal gels to deformation cycles to failure (appearance of cracks, crazes, rips or tears in the gels).

Tensile strength can be determined by extending a selected gel sample to break as measured at 180° U bend around a 5.0 mm mandrel attached to a spring scale. Likewise, tear strength of a notched sample can be determined by propagating a tear as measured at 180° U bend around a 5.0 mm diameter mandrel attached to a spring scale.

Various block copolymers can be obtained which are amorphous, highly rubbery, and exhibiting minimum dynamic hysteresis:

Block copolymer S-EB-S

The monomer butadiene can be polymerized in a ether/hydrocarbon solvent to give a 50/50 ratio of 1,2 poly (butadiene)/1,4 poly(butadiene) and on hydrogenation no long runs of $-CH_2-$ groups and negligible crystallinity, ie, about $(0.5)^4$ or 0.06 or 6% and actual crystallinity of about 3%. Due to the constraints of $T_g$ and minimum hysteresis, conventional S-EB-S have ethylene-butylene ratios of about 60:40 with a crystallinity of about $(0.6)^4$ or 0.129 or 12% and actual crystallinity of about 7.7%.

Block copolymer S-EP-S

The monomer isoprene when polymerized will produce 95% 1,4 poly(isoprene)/5% 3,4 poly(isoprene) and upon hydrogenation will form amorphous, rubbery poly(ethylene-propylene) midblock and no long runs of $-CH_2-$ and no crystallinity.

Mixed block copolymer S-EB/EP-S

The polymerization of a 50/50 mixture of isoprene/butadiene monomers in suitable ether/hydrocarbon solvents to give equal amounts of 1,2 and 1,4 poly(butadiene) on hydrogenation will produce a maximum crystallinity of $(0.25)^4$ or 0.4%. The actual crystallinity would be approximately about 0.2%, which is negligible and results in a good rubbery midblock.

The polymerization of a 80/20 mixture of isoprene/butadiene monomers in suitable ether/hydrocarbon solvents to give equal amounts of 1,2 and 1,4 poly(butadiene) will upon hydrogenation produce a low crystallinity of $(0.10)^4$ or 0.01%. The actual crystallinity would be approximately about 0.006%, which is negligible and results in a good rubbery midblock.

The polymerization of a 20/80 mixture of isoprene/butadiene monomers in suitable ether/hydrocarbon solvents to give equal amounts of 1,2 and 1,4 poly(butadiene) will upon hydrogenation produce a low crystallinity of $(0.4)^4$ or 2.56%. The actual crystallinity would be approximately about 1.53%, which is negligible and results in a good rubbery midblock.

The polymerization of a 20/80 mixture of isoprene/butadiene monomers in suitable ether/hydrocarbon solvents to give a 40:60 ratio of 1,2 and 1,4 poly(butadiene) will upon hydrogenation produce a low crystallinity of $(0.48)^4$ or 5.3%. The actual crystallinity would be approximately about 3.2%, which is negligible and results in a good rubbery midblock.

For purpose of convince and simplicity, the hydrogenated polybutadiene are denoted as follows: -E- denotes at least 85% R-1 units, -B- denotes at least 70% R-2 units, -EB- denotes between 15 and 70% R-2 units, $-EB_n-$ denotes n% R-2 units, and -EP- denotes 90% R-3 units.

Table I below gives the % of units on hydrogenation of polybutadiene/polyisoprene copolymer midblocks

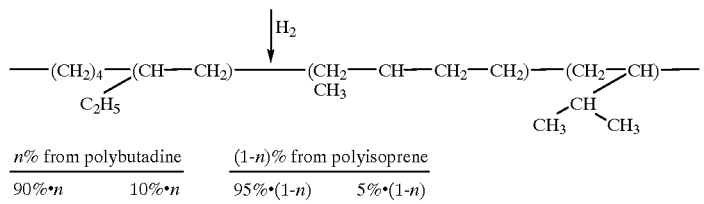

| n% from polybutadine | | (1-n)% from polyisoprene | |
|---|---|---|---|
| 90%•n | 10%•n | 95%•(1-n) | 5%•(1-n) | where n is the mole % polybutadiene in the polybutadiene-polyisoprene starting polymer

| n = | R - 1 | R - 2 | R - 3 | R - 4 |
|---|---|---|---|---|
| 0% | 0% | 0% | 95% | 5% |
| 20% | 18% | 2% | 76% | 4% |
| 40% | 36% | 4% | 57% | 3% |
| 60% | 54% | 6% | 38% | 2% |
| 80% | 72% | 8% | 19% | 1% |
| 100% | 90% | 10% | 0% | 0% | where R - 1 denotes $(-CH_2-)_4$

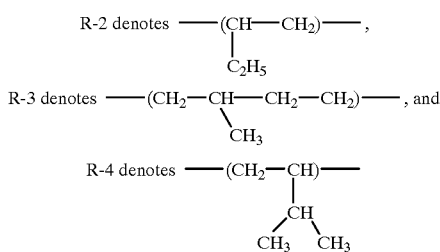

Therefore, the percentage that can crystallize is $[(-CH_2-)_4]^4$ since this is the chance of getting four $(-CH_2-)_4$ units in sequence. The percentage that will crystallize is about 60% of this.

| n = | $(-CH_2-)_4$ | $[(-CH_2-)_4]^4$ | $0.6 \times [(-CH_2-)_4]^n$ |
|---|---|---|---|
| 0% | 0% | 0% | 0% |
| 20% | 18% | 0.1% | 0.06% |
| 40% | 36% | 1.7% | 1.0% |
| 60% | 54% | 8.5% | 5.1% |
| 80% | 72% | 26.9% | 16.1% |
| 100% | 90% | 65.6% | 39.4% |

This applies to polymerization in a hydrocarbon solvent. In an ether (eg, diethylether), the percentage $(-CH_2-)^4$ units will be reduced so that crystallinity will be negligable.

| n = | $(-CH_2-)_4$ | $[(-CH_2-)_4]^4$ | $0.6 \times [(-CH_2-)_4]^n$ |
|---|---|---|---|
| 0% | 0% | 0% | 0% |
| 20% | 5% | 0.0006% | 0.0004% |
| 40% | 10% | 0.01% | 0.006% |
| 60% | 15% | 0.05% | 0.03% |
| 80% | 20% | 0.16% | 0.10% |
| 100% | 25% | 0.39% | 0.23% |

These values are all negligable. There will be no detactable crystallinity in any of these polymer midblocks.

In a mixed ether/hydrocarbon solvent, values will be intermediate, depending on the ratio of ether to hydrocarbon.

The midblocks (Z) of one or more -E-, -B-, -EB-, or -EP- can comprise various combinations of midblocks between the selected end blocks (A); these include: -E-EB-, -E-EP-, -B-EP-, -B-EB-, -E-EP-E-, -E-EB-B-, -B-EP-B-, -B-EB-B-, -E-B-EB-, -E-B-EP-, -EB-EP-, -E-EB-EP-, -E-EP-EB-, -B-EB-EP-, -B-EP-EB-, -E-EP-E-EP-, -E-EP-E-EB-, -B-EP-B-EP-, -B-EB-B-EB-, -B-EB-B-EP-, -E-EB-B-EP-, -E-EP-B-EB-, -E-EP-E-EP-E-, -B-EP-B-EP-B-, -E-EP-E-EB-, -E-EP-E-EP-EB-, -E-EP-E-EP-E-, -E-EP-EB-EP-EB-B- and the like.

The block copolymers of (A-Z-A) can be obtained by sequential synthesis methods followed by hydrogenation of the midblocks. As denoted above, abbreviations are interchangeably used, for example, (S-E-EP-S) denotes poly(styrene-ethylene-ethylene-co-propylene-styrene). Other linear block copolymers (denoted in abbreviations) include the following:

(S-E-EB-S), (S-E-EP-S), (S-B-EP-S), (S-B-EB-S), (S-E-EP-E-S), (S-E-EB-B-S), (S-B-EP-B-S), (S-B-EB-B-S), (S-E-B-EB-S), (S-E-B-EP-S), (S-EB-EP-S), (S-E-EB-EP-S), (S-E-EP-EB-S), (S-B-EB-EP-S), (S-B-EP-EB-S), (S-E-EP-E-EP-S), (S-E-EP-E-EB-S), (S-EP-B-EP-S), (S-B-EB-B-EB-S), (S-B-EB-B-EP-S), (S-E-EB-B-EP-S), (S-E-EP-B-EB-S), (S-E-EP-E-EP-E-S), (S-B-EP-B-EP-B-S), (S-E-EP-E-EB-S), (S-E-EP-E-EP-EB-S) (S-E-EP-E-EP-E-S), (S-E-EP-EB-EP-EB-B-S), (S-E-EP-EB-EP-EB . . . -S) and the like.

The multiblock star-shaped (or radial) copolymers $(A-Z)_n X$ can be obtained by sequential synthesis methods including hydrogenation of selected block copolymers made by polymerizing half of the block copolymers such as SBS or SIS and couple the halves with a coupling agent such as an organic dihalide; or couple with an agent such as SnCl4, which resutls in star-shaped block copolymers (four branches). Coupling with divinyl benzene give block copolymers which are very highly branched. Radial block copolymers suitable for use in forming the crystal gels of the present invention include: $(S-E-EB-S)_n$, $(S-E-EP)_n$, $(S-B-EP)_n$, $(S-B-EB)_n$, $(S-E-EP-E)_n$, $(S-E-EB-B)_n$, $(S-B-EP-B)_n$, $(S-B-EB-B)_n$, $(S-E-B-EB)_n$, $(S-E-B-EP)_n$, $(S-EB-EP)_n$, $(S-E-EB-EP)_n$, $(S-E-EP-EB)_n$, $(S-B-EB-EP)_n$, $(S-B-EP-EB)_n$, $(S-E-EP-E-EP)_n$, $(S-E-EP-E-EB)_n$, $(S-EP-B-EP)_n$, $(S-B-EB-B-EB)_n$, $(S-B-EB-B-EP)_n$, $(S-E-EB-B-EP)_n$, $(S-E-EP-B-EB)_n$, $(S-E-EP-E-EP-E)_n$, $(S-B-EP-B-EP-B)_n$, $(S-E-EP-E-EB)_n$, $(S-E-EP-E-EP-EB)_n$, $(S-E-EP-E-EP-E)_n$, $(S-E-EP-EB-EP-EB-B)_n$ The selected amount of crystallinity in the midblock should be sufficient to achieve improvements in one or more physical properties including improved damage tolerance, improved crack propagation resistance, improved tear resistance, improved resistance to fatigue of the bulk gel and resistance to catastrophic fatigue failure of crystal gel composites, such as between the surfaces of the crystal gel and substrate or at the interfaces of the interlocking material (s) and crystal gel, which improvements are not found in amorphous gels at corresponding gel rigidities.

As an example, when fabric interlocked or saturated with amorphous S-EB-S gels (gel composites) are used as gel liners for lower limb or above the knee prosthesis to reduce pain over pressure areas and give relief to the amputee, the commonly used amorphous gels forming the liners can tear or rip apart during marathon racewalk after 50–70 miles. In extended use, the amorphous gels can rip on the bottom of the liner in normal racewalk training of 40–60 miles over a six weeks period. In such demanding applications, the crystal gels are especially advantageous and is found to have greater tear resistance and resistance to fatigue resulting from a large number of deformation cycles than amorphous gels.

Selected (I) linear block and radial copolymers utilized in forming the crystal gels of the invention are characterized as having an ethylene to butylene midblock ratio (E:B) of about 85:15 to about 65:35. Advantageously, the butylene concentration of the midblock is about 35% or less, more advantageously, about 30% or less, still more advantageously, about 25% or less, especially advantageously, about 20% or less. Advantageously, the ethylene to butylene midblock ratios can range from about 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34 to about 65:35.

The A to Z midblock ratio of the block copolymers suitable for forming crystal gels of the invention can range from about 20:80 to 40:60 and higher. More specifically, the values can be 15:85, 19:81, 20:80, 21:79. 22:78. 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and 52:48.

The crystal gels can optionally comprise selected major or minor amounts of one or more polymers or copolymers (II) provided the amounts and combinations are selected without substantially decreasing the desired properties. The polymers and copolymers can be linear, star-shaped (radial), branched, or multiarm; these including: (SBS) styrene-butadiene-styrene block copolymers, (SIS) styrene-isoprene-styrene block copolymers, low and medium viscosity (S-EB-S) styrene-ethylene-butylene-styrene block copolymers, (S-EP) styrene-ethylene-propylene block copolymers, (S-EP-S) styrene-ethylene/propylene-styrene block copolymers, (S-E-EPS) styrene-ethylene-ethylene/propylene-styrene block copolymers, $(SB)_n$ styrene-butadiene and $(S-EB)_n$, $(S-EB-S)_n$, $(S-E-EP)_n$, $(SEP)_n$, $(SI)_n$ multi-arm, branched or star-shaped copolymers, polyethyleneoxide (EO), poly(dimethylphenylene oxide), teflon (TFE, PTFE, PEA, FEP, etc), optical clear amorphous copolymers based on 2,2-bistrifluoromethyl-4,5-difuoro-1,3-dioxole (PDD) and tetrafluoroethylene (TFE), maleated S-EB-S block copolymer, polycarbonate, ethylene vinyl alcohol copolymer, and the like. Still, other (II) polymers include homopolymers which can be utilized in minor amounts; these include: polystyrene, polydimethylsiloxane, polyolefins such as polybutylene, polyethylene, polyethylene copolymers, polypropylene,and the like. Polyurethane elastomers based on saturated hydrocarbon diols (Handlin, D., Chin. S., and Masse. M., et al. "POLYURETHANE ELASTOMERS BASED ON NEW SATURATED HYDROCARBON DIOLS" Published Society of Plastics Industry, Polyurethane Division, Las Vegas, Oct. 23, 1996) are also suitable for use in blending with the block copolymers (I) used in forming the crystal gels of the invention. Such saturated hydrocarbon diols include hydroxyl terminated oligomers of poly(ethylene-butylene) (EB), poly(ethylene-propylene) (EP),-E-EB-, -E-EP-, -B-EP-, -B-EB-, -E-EP-E-, -E-EB-B-, -B-EP-B-, -B-EB-B-, -E-B-EB-, -E-B-EP-, -EB-EP-, -E-EB-EP-, -E-EP-EB-, -B-EB-EP-, -B-EP-EB-, -E-EP-E-EP-, -E-EP-E-EB-, -B-EP-B-EP-, -B-EB-B-EB-, -B-EB-B-EP-, -E-EB-B-EP-, -E-EP-B-EB-, -E-EP-E-EP-E-, -B-EP-B-EP-B-, -E-EP-E-EB-, -E-EP-E-EP-EB-, -E-EP-E-EP-E-, -E-EP-EB-EP-EB-B- and the like. As an example, thermoplastic polyurethane made with isocyanates and chain extenders such as TMPD and BEPD from saturated hydrocarbon diol KLP L-2203 having a hard segment contents of 22% exhibits clean phase separation of the hard and soft segments with glass a transition of −50° C. KLP L-2203 based TPU's can be mixed with the crystalline block copolymers to form soft crystal gels within the gel rigidity ranges of the invention.

Suitable polyolefins include polyethylene and polyethylene copolymers such as Dow Chemical Company's Dowlex 3010, 2021D, 2038, 2042A, 2049, 2049A, 2071, 2077, 2244A, 2267A; Dow Affinity ethylene alpha-olefin resin PL-1840, SE-1400, SM-1300; more suitably: Dow Elite 5100, 5110, 5200, 5400, Primacor 141-XT, 1430, 1420, 1320, 3330, 3150, 2912, 3340, 3460; Dow Attane (ultra low density ethylene-octene-1 copolymers) 4803, 4801, 4602, The conventional term "major" means about 51 weight percent and higher (e.g. 55%, 60%, 65%, 70%, 75%, 80% and the like) and the term "minor" means 49 weight percent and lower (e.g. 2%, 5%, 10%, 15%, 20%, 25% and the like).

Example of (II) polymers, copolymers, and blends include: (a) Kraton G 1651, G 1654X; (b) Kraton G 4600; (c) Kraton G 4609; other suitable high viscosity polymer and oils include: (d) Tuftec H 1051; (e) Tuftec H 1041; (f) Tuftec H 1052; (g) Kuraray S-E-EP-S 4033; (h) Kuraray S-EB-S 8006; (i) Kuraray SEPS 2005; (j) Kuraray SEPS 2006, and (k) blends (polyblends) of (a)–(h) with other polymers and copolymers include: (1) S-EB-S/SBS; (2) S-EB-S/SIS; (3) S-EB-S/(SEP); (4) S-EB-S/(SEB),.; (5) S-EB-S/(SEB),.; (6) S-EB-S/(SEP)$_n$; (7) S-EB-S/(SI)$_n$; (8) S-EB-S/(SI) multi-arm; (9) S-EB-S/(SEB)$_n$; (10) $(SEB)_n$ star-shaped copolymer; (11) s made from blends of (a)–(k) with other homopolymers include: (12) S-EB-S/polystyrene; (13) S-EB-S/polybutylene; (14) S-EB-S/poly-ethylene; (14) S-EB-S/polypropylene; (16) SEP/S-EB-S, (17) SEP/SEPS, (18) SEP/SEPS/SEB, (19), SEPS/S-EB-S/SEP, (20), SEB/S-EB-S (21), EB-EP/S-EB-S (22), S-EB-S/EB (23), S-EB-S/EP (24), (25) $(SEB)_n$ s, (26) $(SEP)_n$, (27) Kuraray 2007 (SEPS), (28) Kuraray 2002, (SEPS), (29) Kuraray 4055 (S-E-EP-S) (30) Kuraray 4077 (S-E-EP-S) (31) Kuraray 4045 (S-E-EP-S) (32) (S-EB-EP)$_n$, (33) $(SEB)_n$, (34) EPDM, (35) EPR, (36) EVA, (37) coPP, (38) EMA, (39) EEA, (40) DuPont Teflon AF amorphous fluoropolymers, (41) Dow polydimethylsiloxane, (42) maleated S-EB-S (maleation level 2–30%), (43) $(EP)_n$ and the like.

Representative examples of commercial elastomers that can be combined with the block copolymers (I) described above include: Shell Kratons D1101, D1102, D1107, D1111, D1112, D1113X, D1114X, D1116, D1117, D1118X, D1122X, D1125X, D1133X, D1135X, D1184, D1188X, D1300X, D1320X, D4122, D4141, D4158, D4240, G1650, G1652, G1657, G1701X, G1702X, G1726X, G1750X, G1765X, FG1901X, FG1921X, D2103, D2109, D2122X, D3202, D3204, D3226, D5298, D5999X, D7340, G1650, G1651, G1652, G4609, G4600, G1654X, G2701, G2703, G2705, G1706, G2721X, G7155, G7430, G7450, G7523X, G7528X, G7680, G7705, G7702X, G7720, G7722X, G7820, G7821X, G7827, G7890X, G7940, FG1901X and FG1921X. Kuraray's SEP, SEPS, S-EB-S, S-EB-EP-S, S-E-EP-S (hydrogenated styrene isoprene/butadiene block copolymers, more specifically, hydrogenated styrene block polymer with 2-methyl-1,3-butadiene and 1,3-butadiene) Nos. 1001, 1050, 2027, 2003, 2006, 2007, 2008, 2023, 2043, 2063, 2050, 2103, 2104, 2105, 4033, 4045, 4055, 4077, 8004, 8006, 8007, H-VS-3 (S-V-EP)N, and the like.

The amorpous S-EB-S and (S-EB)$_n$ (II) copolymers can have a broad range of styrene to ethylene-butylene ratios (S:EB) of about 20:80 or less to about 40:60 or higher. The S:EB weight ratios can range from lower than about 20:80 to above about 40:60 and higher. More specifically, the values can be 15:85, 19:81, 20:80, 21:79. 22:78. 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 52:48 and etc. Other ratio values of less than 19:81 or higher than 51:49 are also possible. Broadly, the styrene block to elastomeric block ratio of the high viscosity liner and star copolymers is about 20:80 to about 40:60 or higher, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and still more preferably about 30:70.

The Brookfield Viscosity of a 5 weight percent solids solution in toluene at 30° C. of 2006, 4045, 4055, 4077 typically range about 20–35, about 25–150, about 60–150, about 200–400 respectively. Typical Brookfield Viscosities of a 10 weight percent solids solution in toluene at 30° C. of 1001, 1050, 2007, 2063, 2043, 4033, 2005, 2006, are about 70, 70, 17, 29, 32, 50, 1200, and 1220 respectively. Typical Brookfield Viscosity of a 25 weight percent solids solution in toluene at 25° C. of Kraton D1101, D1116, D1184, D1300X, G1701X, G1702X are about 4000, 9000, 20000, 6000, 50000 and 50000 cps respectively. Typical Brookfield Viscosity of a 10 weight percent solids solution in toluene at 25° C. of G1654X is about 370 cps. The Brookfield Viscosities of a 20 and 30 weight percent solids solution in toluene at 30° C. of H-VS-3 are about 133 cps and 350 cps respectively.

Suitable block copolymers (II) and their typical viscosities are further described. Shell Technical Bulletin SC:1393-92 gives solution viscosity as measured with a Brookfield model RVT viscometer at 25° C. for Kraton G 1654X at 10% weight in toluene of approximately 400 cps and at 15% weight in toluene of approximately 5,600 cps. Shell publication SC:68-79 gives solution viscosity at 25° C. for Kraton G 1651 at 20 weight percent in toluene of approximately 2,000 cps. When measured at 5 weight percent solution in toluene at 30° C., the solution viscosity of Kraton G 1651 is about 40. Examples of high viscosity S-EB-S triblock copolymers includes Kuraray's S-EB-S 8006 which exhibits a solution viscosity at 5 weight percent at 30° C. of about 51 cps. Kuraray's 2006 SEPS polymer exhibits a viscosity at 20 weight percent solution in toluene at 30° C. of about 78,000 cps, at 5 weight percent of about 27 cps, at 10 weight percent of about 1220 cps, and at 20 weight percent 78,000 cps. Kuraray SEPS 2005 polymer exhibits a viscosity at 5 weight percent solution in toluene at 30° C. of about 28 cps, at 10 weight percent of about 1200 cps, and at 20 weight percent 76,000 cps. Other grades of S-EB-S, SEPS, (SEB)$_n$, (SEP)$_n$ polymers can also be utilized in the present invention provided such polymers exhibits the required high viscosity. Such S-EB-S polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene (S:EB) weight ratios for the Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values. In the case of Kuraray's S-EB-S polymer 8006 the S:EB weight ratio is about 35:65. In the case of Kuraray's 2005 (SEPS), and 2006 (SEPS), the S:EP weight ratios are 20:80 and 35:65 respectively. The styrene to ethylene-ethylene/propylene (S:E-EP) ratios of Kuraray's SEPTON 4045, 4055, and 4077 are typically about 37.6, 30, 30 respectively. More typically the (S:E-EP) and (S:EP) ratios can vary broadly much like S:EB ratios of S-EB-S and (SEB), from less than 19:81 to higher than 51:49 (as recited above) are possible. It should be noted that multiblock copolymers including SEPTON 4045, 4055, 4077 and the like are described in my cited copending parent applications and are the subject matter of related inventions.

The block copolymers (II) such as Kraton G 1654X having ratios of 31:69 or higher can be used and do exhibit about the same physical properties in many respects to Kraton G 1651 while Kraton G 1654X with ratios below 31:69 may also be use, but they are less advantageous due to their decrease in the desirable properties of the final gel.

Plasticizers (III) particularly advantageous for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight.

Examples of representative commercially available plasticizing oils include Amoco® polybutenes, hydrogenated polybutenes, polybutenes with epoxide functionality at one end of the polybutene polymer, liquid poly(ethylene/butylene), liquid hetero-telechelic polymers of poly(ethylene/butylene/styrene) with epoxidized polyisoprene and poly(ethylene/butylene) with epoxidized polyisoprene: Example of such polybutenes include: L-14 (320 Mn), L-50 (420 Mn), L-100 (460 Mn), H-15 (560 Mn), H-25 (610 Mn), H-35 (660 Mn), H-50 (750 Mn), H-100 (920 Mn), H-300 (1290 Mn), L-14E (27–37 cst @ 100° F. Viscosity), H-300E (635–690 cst @ 210° F. Viscosity), Actipol E6 (365 Mn), E16 (973 Mn), E23 (1433 Mn), Kraton L-2203 and Kraton L-1203, EKP-206, EKP-207, HPVM-2203 and the like. Example of various commercially oils include: ARCO Prime (55, 70, 90, 200, 350, 400 and the like), Duraprime and Tufflo oils (6006, 6016, 6016M, 6026, 6036, 6056, 6206, etc) , other white mineral oils include: Bayol, Bernol, American, Blandol, Drakeol, Ervol, Gloria, Kaydol, Litetek, Lyondell (Duraprime 55, 70, 90, 200, 350, 400, etc), Marcol, Parol, Peneteck, Primol, Protol, Sontex, Witco brand white oils including RR-654-P and the like. Generally, plasticizing oils with average molecular weights less than about 200 and greater than about 700 may also be used (e.g., H-300 (1290 Mn)).

Comparisons of oil extended S-EB-S triblock copolymers have been described in Shell Chemical Company Technical Bulletin SC:1102-89 (April 1989) "KRATON® THERMOPLASTIC RUBBERS IN OIL GELS" which is incorporated herein by reference.

The crystal gels can be made non-adhearing, non-sticking, (non-tacky), by incorporating an advantage amount of stearic acid (octadecanoic acid), metal stearates (e.g., calcium stearate, magnesium stearate, zinc stearate, etc.), polyethylene glycol distearate, polypropylene glycol ester or fatty acid, and polytetramethylene oxide glycol disterate, waxes, stearic acid and waxes, metal stearate and waxes, metal stearate and stearic acid. The use of stearic acid alone do not reduce tack. The amount of stearic acid is also important. As an example, ratio of 200 grams stearic acid to 2,000 gram of S-EB-S (a ratio of 0.1) will result in spotted tack reduction on the surface of the gel. A ratio of 250 to 2,000 will result in spotted crystallized stearic acid regions on the surface of the gel or spotted tack reduction. A ratio of 300 to 2,000 will result in complete tack reduction with large stearic acid crystallized regions on the surface of the gel. When microcrystalline waxes are incorporated together with stearic acid, the crystallization of stearic acid completely disappears from the surface of the gel. For example excellent result is achieved with 200 grams of stearic acid, 150 grams of microcrystalline wax and 2,000 grams of S-EB-S. The same excellent result is achieved when S-EB-S is adjusted to 3,000 grams, 4,000 grams, etc. The same result is achieved with (I) copolymers as well as in combination with polymers (II) such as SEPS, S-EB-EP-S, (S-EB-EP)$_n$, (SEB)$_n$, (SEP)$_n$ polymers.

The crystal gels can also contain useful amounts of conventionally employed additives such as stabilizers, antioxidants, antiblocking agents, colorants, fragrances, flame retardants, flavors, other polymers in minor amounts and the like to an extend not affecting or substantially decreasing the desired properties. Additives useful in the crystal gel of the present invention include: tetrakis [methylene 3,-(3'5'-di-tertbutyl- 4"-hydroxyphenyl) propionate] methane, octadecyl 3-(3", 5"-di-tert-butyl-4"-hydroxyphenyl) propionate, distearyl-pentaerythritol-diproprionate, thiodiethylene bis-(3,5-ter-butyl-4-hydroxy) hydrocinnamate, (1,3,5-trimethyl-2,4,6-tris[3,5-di-tert-butyl-4-hydroxybenzyl] benzene), 4,4"-methylenebis(2,6-di-tert-butylphenol), steraric acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, calcium sterate, other metal sterates, waxes (e.g., polyethylene, polypropylene, microcrystalline, carnauba, paraffin, montan, candelilla, beeswax, ozokerite, ceresine, and the like), teflon (TFE, PTFE, PEA, FEP, etc), polysiloxane, etc. The crystal gel can also contain metallic pigments (aluminum and brass flakes), TiO2, mica, fluorescent dyes and pigments, phosphorescent pigments, aluminatrihydrate, antimony oxide, iron oxides (Fe3O4, —Fe2O3, etc.), iron cobalt oxides, chromium dioxide, iron, barium ferrite, strontium ferrite and other magnetic particle materials, molybdenum, silicones, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on Magnetic Materials, Publication NMAB-426, National Academy Press (1985) is incorporated herein by reference.

The crystal gels can also be made into composites. The crystal gels can be casted unto various substrates, such as open cell materials, metals, ceramics, glasses, and plastics, elastomers, fluropolymers, expanded fluropolymers, Teflon (TFE, PTFE, PEA, FEP, etc), expanded Teflon, spongy expanded nylon, etc.; the molten crystal gel is deformed as it is being cooled. Useful open-cell plastics include: polyamides, polyimides, polyesters, polyisocyanurates, polyisocyanates, polyurethanes, poly(vinyl alcohol), etc. Suitable open-celled Plastic (sponges) are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

The crystal gels denoted as "G" can be physically interlocked with a selected material denoted as "M" to form composites as denoted for simplicity by their combinations $G_nG_n$, $G_nG_nG_n$, $G_nM_n$, $G_nM_nG_n$, $M_nG_nM_n$, $M_nG_nG_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_n$ $G_nM_n$, $G_nM_nG_nG_n$, $G_nG_nM_n$, $G_nM_nG_nM_nM_n$, MnGnMnGnMnGn, $G_nG_nM_nM_nG_n$, $G_nG_nM_nG_nM_nG_n$, and the like or any of their permutations of one or more $G_n$ with $M_n$ and the like, wherein when n is a subscript of M, n is the same or different selected from the group consisting of paper, foam, plastic, fabric, metal, concrete, wood, glass, ceramics, synthetic resin, synthetic fibers or refractory materials and the like; wherein when n is a subscript of G, n denotes the same or a different gel rigidity of from about 2 gram to about 1,800 gram Bloom). The crystal gels of the composites are formed from copolymers (I), polymers (II), and plasticizers (III) described above.

Sandwiches of crystal gel-material (i.e., crystal gel-material-crystal gel or material-crystal gel-material, etc.) are useful as dental floss, shock absorbers, acoustical isolators, vibration dampers, vibration isolators, and wrappers. For example the vibration isolators can be use under research microscopes, office equipment, tables, and the like to remove background vibrations. The tear resistance nature of the instant crystal gels are superior in performance to amorphous block copolymer gels which are much less resistance to crack propagation caused by long term continue dynamic loadings.

The crystal gels are prepared by blending together the components including other additatives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amounts of multiblock copolymers (I) and polymer (II) used. These components blend easily in the melt and a heated vessel equipped with a stirrer is all that is required. Small batches can be easily blended in a test tube using a glass stirring rod for mixing. While conventional large vessels with pressure and/or vacuum means can be utilized in forming large batches of the instant crystal gels in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than 10 rpm to about 40 rpm or higher.

The crystal gel articles can be formed by blending, injection molding, extruding, spinning, casting, dipping and other conventional methods. For example, Shapes having various cross-section can be extruded. The crystal gels can also be formed directly into articles or remelted in any suitable hot melt applicator and extruded into shaped articles and films or spun into threads, strips, bands, yarns, or other shapes. With respect to various shapes and yarn, its size are conventionally measured in denier (grams/9000 meter), tex (grams/1000 meter), and gage (1/2.54 cm). Gage, tex, denier can be converted as follows: tex=denier/9=specific gravity (2135/gage), for rectangular cross section, tex=specific gravity (5806× 103) (th) (w) /9, where th is the thickness and w the width of the strip, both in centimeters. General descriptions of (1) block copolymers, (2) elastomeric fibers and conventional (3) gels are found in volume 2, starting at pp. 324–415, volume 6, pp 733–755, and volume 7, pp. 515 of *ENCYCLOPEDIA OF POLYMER SCIENCE AND ENGINEERING*, 1987 which volumes are incorporated herein by reference.

The crystal gels are excellent for cast molding and the molded products have various excellent characteristics which cannot be anticipated form the properties of the raw components. Other conventional methods of forming the composition can be utilized.

Not only do the crystal gels have all the desirable combination of physical and mechanical properties substantially similar to high viscosity amorphous S-EB-S gels such as high elongation at break of at least 1,600%, ultimate tensile strength of about $8 \times 10^5$ dyne/cm$^2$ and higher, low elongation set at break of substantially not greater than about 2%, substantially about 100% snap back when extended to 1,200% elongation, and a gel rigidity of substantially from about 2 gram to about 1,800 gram Bloom and higher, the crystal gels of the present invention exhibit improved tear resistance and resistance to fatigue not obtainable from amorphous S-EB-S gels at corresponding gel rigidities.

The crystal gels of the present invention exhibit one or more of the following properties. These are: (1) tensile strength of about $8 \times 10^5$ dyne/cm$^2$ to about $10^7$ dyne/cm$^2$ and greater; (2) elongation of less than about 1,600% to about 3,000% and higher; (3) elasticity modules of about $10^4$ dyne/cm$^2$ to about $10^6$ dyne/cm$^2$ and greater; (4) shear modules of about $10^4$ dyne/cm$^2$ to about $10^6$ dyne/cm$^2$ and greater as measured with a 1, 2, and 3 kilogram load at 23°0 C.; (5) gel rigidity of about less than about 2 gram Bloom to about 1,800 gram Bloom and higher as measured by the gram weight required to depress a gel a distance of 4 mm with a piston having a cross-sectional area of 1 square cm at 23° C.; (6) tear propagation resistance greater than the tear resistance of amorphous S-EB-S gels at corresponding gel rigidities; (7) resistance to fatigue greater than the fatigue resistance of amorphous S-EB-S gels at corresponding gel rigidities; (8) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C.

The crystal gel articles molded from the instant crystal gels have additional important advantages in that they end-use performance properties are greater than amorphous S-EB-S gels in that they are more resistant to cracking, tearing, crazing or rupture in flexural, tension, compression, or other deforming conditions of use. Like amorphous gels, the molded articles made from the instant composition possess the intrinsic properties of elastic memory enabling the articles to recover and retain its original molded shape after many extreme deformation cycles.

Because of their improved tear resistance and improved resistance to fatigue, the crystal gels of the present invention achieve greater performance than amorphous gels in low frequency vibration applications, such as viscoelastic layers in constrained-layer damping of mechanical structures and goods, as viscoelastic layers used in laminates for isolation of acoustical and mechanical noise, as anti-vibration elastic support for transporting shock sensitive loads, as vibration isolators for an optical table, as viscoelastic layers used in wrappings, enclosures and linings to control sound, as compositions for use in shock and dielectric encapsulation of optical, electrical, and electronic components.

Because of their improved tear resistance and improved resistance to fatigue, the crystal gels are more useful as molded shape articles for use in medical and sport health care, such use include therapeutic hand exercising grips, dental floss, crutch cushions, cervical pillows, bed wedge pillows, leg rest, neck cushion, mattress, bed pads, elbow padding, dermal pads, wheelchair cushions, helmet liner, cold and hot packs, exercise weight belts, traction pads and belts, cushions for splints, slings, and braces (for the hand, wrist, finger, forearm, knee, leg, clavicle, shoulder, foot, ankle, neck, back, rib, etc.), and also soles for orthopedic shoes. Other uses include various shaped articles as toys, optical uses (e.g., cladding for cushioning optical fibers from bending stresses) and various optical devices, as lint removers, dental floss, as tips for swabs, as fishing bate, as a high vacuum seal (against atmosphere pressure) which contains a useful amount of a mineral oil-based magnetic fluid particles, etc. Moreover, the casted, extruded, or spun threads, strips, yarns, tapes can be weaved into cloths, fine or coarse fabrics.

The crystal gels can be formed in any shape; the original shape can be deformed into another shape (to contact a regular or irregular surface) by pressure and upon removal of the applied pressure, the composition in the deformed shape will recover back to its original shape.

As an example of the versatility of use of the instant crystal gels, a hand exerciser can be made in any shape so long as it is suitable for use as a hand exerciser: a sphere shape, a cube shape, a rectangular shape, etc. Likewise, a wheelchair cushion can be made from the composition in any shape, so long as it meets the needs of the user of the cushion. For example, a cushion can be made by forming the composition into a selected shape matching the contours of the specific body part or body region. The composition can be formed into any desired shaped, size and thickness suitable as a cushion; the shaped composition can be additionally surrounded with film, fabric, foam, or any other desired material or combinations thereof. Moreover, the composition can be casted onto such materials, provided such materials substantially maintain their integrity (shape, appearance, texture, etc.) during the casting process. The same applies for brace cushions, liners, linings and protective coverings for the hand, wrist, finger, forearm, knee, leg, etc.

Because of their improved tear resistance and resistance to fatigue, the crystal gels exhibit versatility as balloons for medical uses, such as balloon for valvuloplasty of the mitral valve, gastrointestinal balloon dilator, esophageal balloon dilator, dilating balloon catheter use in coronary angiogram and the like. Since the crystal gels are more tear resistant, they are especially useful for making condoms, toy balloons, and surgical and examination gloves. As toy balloons, the crystal gels are safer because it will not rupture or explode when punctured as would latex balloons which often times cause injures or death to children by choking from pieces of latex rubber. The crystal gels are advantageously useful for making gloves, thin gloves for surgery and examination and thicker gloves for vibration damping which prevents damage to blood capillaries in the fingers and hand caused by handling strong shock and vibrating equipment.

Other uses include self sealing enclosures for splicing electrical and telephone cables and wires. For example, the crystal gels can be pre-formed into a small diameter tubing within an outer elastic tubing, both the internal crystal gel tubing and external elastic tubing can be axially expanded and fixed in place by a removable continuous retainer. Upon insertion of a spliced pair or bundle of cables or wires, the retainer can be removed, as the retainer is removed, the crystal gel and elastic tubing impinges onto the inserted cables or wires splices, thereby sealing the electrical splices against weather, water, dirt, corrosives and shielding the splice from external abuse. The enclosure is completed without the use of heat or flame as is conventionally performed.

Because of their improved resistance to tearing, the crystal gels do not tear as readily as amorphous gels when used as dental floss. The dental floss can be almost any shape so long as it is suitable for dental flossing. A thick shaped piece of the composition can be stretched into a thin shape and used for flossing. A thinner shaped piece would require less stretching, etc. For purposes of dental flossing, while flossing between two closely adjacent teeth, especially between two adjacent teeth with substantial contact points and more especially between two adjacent teeth with substantial amalgam alloy metal contact points showing no gap between the teeth, it is critical that the crystal gel resist tearing, shearing, and crazing while being stretched to a high degree in such situations. For example, dental crystal gel floss can take the form of a disk where the segments of the circumference of the disk is stretched for flossing between the teeth. Other shaped articles suitable for flossing include threads, strips, yarns, tapes, etc., mentioned above.

In order for crystal gels to be useful as a dental floss, it must overcome the difficult barriers of high shearing and high tearing under extreme elongation and tension loads. The difficulties that the crystal gels must overcome during flossing can be viewed as follows: during the action of flossing, the crystal gel is stretched from no less than about 200% to about 1,100% or higher, the crystal gel floss is deformed as it is pulled down with tearing action between the contacting surfaces of the teeth, then, the wedge of crystal gel floss is sheared between the inner contacting surfaces of the teeth, and finally, the elongated wedged of crystal gel floss is pulled upwards and out between the surfaces of the teeth. The forces encountered in the act of flossing are: tension, shearing, tearing under extreme tension.

The use of crystal gels advances the flossing art by providing strong, soft, and more tear resistant gels than amorphous gels. Floss made from the crystal gels has many advantages over conventional dental floss such as regular and extra fine waxed and unwaxed nylon floss, spongy nylon fiber floss, and waxed and unwaxed expanded and unexpended teflon floss. Such conventional floss are not recommended for use by children, since a slip or sudden snap in forcing the floss between the teeth may cause injury to the gums which often times results in bleeding. For sensitive gums and inflamed gums which has become red and puffy, it is difficult to floss at, near, and below the gumline. The soft crystal gel floss with softness substantially matching the softness of the gums are of great advantage for use by children and for flossing teeth surrounded by sensitive and tender gums.

In all cases, the tear strength of crystal gels are higher than that of amorphous gels. The rigidities of the crystal gels for use as dental floss advantageously should be selected to exhibit a propagating tear force (when propagating a tear as measured at 180° U bend around a 5.0 mm diameter mandrel attached to a spring scale) of at least about 1 Kg/cm, more advantageously at least 2 Kg/cm, and still more advantageously of about 3 Kg/cm and higher. For any gel to be considered useful for flossing, the gels should exhibit tear strengths of at least 2 Kg/cm and higher, advantageously of at least 4 Kg/cm and higher, more advantageously of at least 6 Kg/cm and higher, exceptionally more advantageously of at least 8 Kg/cm and higher. Typically, the tear propagation strength should range from about 5 Kg/cm to about 20 Kg/cm and higher, more typically from about less than 5 Kg/cm to about 25 Kg/cm and higher, especially more typically form about less than 6 Kg/cm to about 30 Kg/cm and higher, and exceptionally more typically from about less than 8 Kg/cm to about 35 Kg/cm and higher.

For any gel to be considered useful for flossing, the gels, critically, should advantageously exhibit a propagating tension tear force (when a cylindrical sample is notched and a tear is initiated at the notched area and propagated past its maximum cylindrical diameter by length-wise stretching of the cylindrical sample) of at least about 1 Kg/cm, more advantageously at least 2 Kg/cm, and still more advantageously of about 4 Kg/cm and higher. Although the crystal gels of the present invention have improved tear resistance and resistance to fatigue greater than the amorphous gels at corresponding gel rigidities, the high and ultra-high tear resistant gels of my other related parent and c-i-p applications typically will exhibit even higher tear resistance values.

While advantageous components and formulation ranges based on the desired properties of the crystal gels have been disclosed herein. Persons of skill in the art can extend these ranges using appropriate material according to the principles discussed herein. All such variations and deviations which rely on the teachings through which the present invention has advanced the art are considered to be within the spirit and scope of the present invention.

The invention is further illustrated by means of the following illustrative embodiments, which are given for purpose of illustration only and are not meant to limit the invention to the particular components and amounts disclosed.

EXAMPLE I

Gels of 100 parts of high viscosity linear Kraton G1651 (amorphous S-EB-S), Septon 8006 (amorphous S-EB-S), and a high viscosity radial amorphous midblock segment $(SEB)_n$ triblock copolymers and 1,600, 1,200, 1,000, 800, 600, 500, 450, 300, 250 parts by weight of Duraprime 200 white oil (plasticizer) are melt blended and samples molded, the bulk gel rigidities are found to be within the range of 2 to 1,800 gram Bloom and the tensile strength, notched tear strength, and resistance to fatigue are found to decrease with increase amounts of plasticizers.

EXAMPLE II

Example I is repeated using high viscosity crystalline midblock segment linear S-EB-S and radial $(SEB)_n$ triblock copolymers with ethylene to butylene midblock ratios (E:B) of 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, and 70:30 in combination with an equal amount of amorphous S-EB-S having (E:B) ratio of about 60:40, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE III

Gels of 100 parts of Kraton G1651 (amorphous S-EB-S), Septon 8006 (amorphous S-EB-S)$_n$ and a high viscosity amorphous midblock segment (SEB)$_n$ linear and radial triblock copolymers, 1,600, 1,200, 1,000, 800, 600, 500, 450, 300, 250 parts by weight of Duraprime 200 white oil (plasticizer), and 10 parts of Dow polydimethylsiloxane are melt blended and samples molded, the bulk gel rigidities are found to be within the range of 2 to 1,800 gram Bloom and the tensile strength, notched tear strength, and resistance to fatigue are found to decrease with increase amounts of plasticizers.

EXAMPLE IV

Gels of 100 parts of Kraton G1651 (amorphous S-EB-S), Septon 8006 (amorphous S-EB-S), and a high viscosity amorphous midblock segment (SEB)$_n$ linear and radial triblock copolymers, 1,600, 1,200, 1,000, 800, 600, 500, 450, 300, 250 parts by weight of Duraprime 200 white oil (plasticizer), and 2 parts of Dupont Teflon AF 1600 are melt blended and samples molded, the bulk gel rigidities are found to be within the range of 2 to 1,800 gram Bloom and the tensile strength, notched tear strength, and resistance to fatigue are found to decrease with increase amounts of plasticizers.

EXAMPLE V

Example III is repeated using high viscosity crystalline midblock segment linear S-EB-S and radial (SEB)N triblock copolymers with ethylene to butylene midblock ratios (E:B) of 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, and 70:30 in combination with an equal amount of amorphous S-EB-S having (E:B) ratio of about 60:40, the bulk gel rigidities are found to be within the range of 2 gram to 1,800 gram Bloom and the notched tear strength and resistance to fatigue of the gel at corresponding rigidities are found to be greater than that of amorphous gels of Example III.

EXAMPLE VI

Example IV is repeated using high viscosity crystalline midblock segment linear S-EB-S and radial (SEB)$_n$ triblock copolymers with ethylene to butylene midblock ratios (E:B) of 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, and 70:30 in combination with an equal amount of amorphous S-EB-S having (E:B) ratio of about 60:40, the bulk gel rigidities are found to be within the range of 2 gram to 1,800 gram Bloom and the notched tear strength and resistance to fatigue of the gel at corresponding rigidities are found to be greater than that of amorphous gels of Example IV.

EXAMPLE VII

Gels of 100 parts of high viscosity linear (S-EB-S), (S-EP-S), (S-B-EP-S), (S-B-EB-S),(S-B-EP-B-S), (S-B-EB-B-S), (S-B-EB-EP-S), (S-B-EP-EB-S), (S-EB-EP-S), (S-EP-B-EP-S), (S-B-EB-B-EB-S), (S-EB-B-EP-S) and (S-B-EP-B-EP-B-S) block copolymers and 1,600, 1,200, 1,000, 800, 600, 500, 450, 300, 250 parts by weight of Duraprime 200 white oil (plasticizer) are each melt blended and samples molded, the bulk gel rigidities are found to be within the range of 2 to 1,800 gram Bloom and the tensile strength, notched tear strength, and resistance to fatigue are found to decrease with increase amounts of plasticizers.

EXAMPLE VIII

Gels of 100 parts of high viscosity linear (S-EB$_{45}$-EP-S), (S-E-EB$_{25}$-S), (S-EP-E-EP-S), (S-E-EB-S), (S-E-EP-S), (S-E-EP-E-S), (S-E-EB-B-S), (S-E-B-EB-S), (S-E-B-EP-S), (S-E-EB-EP-S), (S-E-EP-EB-S), (S-E-EP-E-EP-S), (S-E-EP-E-EB-S), (S-E-EB-B-EP-S), (S-E-EP-B-EB-S), (S-E-EP-E-EP-E-S), (S-E-EP-E-EB-S), (S-E-EP-E-EP-EB-S), (S-E-EP-E-EP-E-S), and (S-E-EP-EB-EP-EB-B-S) block copolymers and 1,600, 1,200, 1,000, 800, 600, 500, 450, 300, 250 parts by weight of Duraprime 200 white oil (plasticizer) are each melt blended and samples molded, the bulk gel rigidities are found to be within the range of 2 to 1,800 gram Bloom and the tensile strength, notched tear strength, and resistance to fatigue are found to be greater than that of amorphous gels of Example VII.

EXAMPLE IX

Example VIII is repeated and minor amounts of 2, 5, 10 and 15 parts of the following polymers are formulated with each of the triblock copolymers: styrene-butadiene-styrene block copolymers, styrene-isoprene-styrene block copolymers, low viscosity styrene-ethylene-butylene-styrene block copolymers, styrene-ethylene-propylene block copolymers, styrene-ethylene-propylene-styrene block copolymers, styrene-butadiene, styrene-isoprene, polyethyleneoxide, poly(dimethylphenylene oxide), polystyrene, polybutylene, polyethylene, polypropylene, high ethylene content EPDM, amorphous copolymers based on 2,2-bistrifluoromethyl-4,5-difuoro-1,3-dioxole/tetrafluoroethylene. The bulk gel rigidities of each of the formulations are found to be within the range of 2 gram to 2,000 gram Bloom and the notched tear strength and resistance to fatigue of the gels at corresponding rigidities are found to be greater than that of amorphous gels of Example I formulated with corresponding amounts of the same polymers.

EXAMPLE X

Molten gels of Examples I–IX are formed into composites with paper, foam, plastic, elastomers, fabric, metal, concrete, wood, glass, ceramics, synthetic resin, synthetic fibers, and refractory materials and the resistance to fatigue of the composite-crystal gels at corresponding rigidities are found to be greater than that of the composite-amorphous gels.

EXAMPLE XI

Three cm thick sheets of each of the crystal gels of Example II and VIII and the amorphous gels of Example I and VII are tested by repeatedly displacing the sheets to a depth of 1 cm using a 10 cm diameter smooth (water soaked) wood plunger for 1,000, 5,000, 10,000, 25,000, 50,000, and 100,000 cycles. The sheets of crystal gels are found capable of exhibiting greater fatigue resistance than the sheets of amorphous gels at corresponding rigidities.

While preferred components and formulation ranges have been disclosed herein persons of skill in the art can extend these ranges using appropriate material according to the principles discussed herein. Furthermore, Crystalline midblock segment block polymers can be use in blending with other engineering plastics and elastomeric polymers to make alloyed compositions having improved impact and tear resistance properties. All such variations and deviations which rely on the teachings through which the present invention has advanced the art are considered to be within the spirit and scope of the present invention.

What I claim is:

1. An improved gelatinous composition comprising: a crystal gel formed from (I) 100 parts by weight of one or more linear, branched, star-shaped (radial), or multiarm block copolymers or mixtures of two or more such block copolymers, said block copolymers having one or more midblocks, said midblocks comprising one or more substantially crystalline polyethylene midblocks and with one or more or without amorphous midblocks; optionally in combination with a selected amount of one or more of a (II) polymer or copolymer, and selected amounts of a plasticizing oil (III) sufficient to achieve gel rigidities of from less than about 2 gram Bloom to about 1,800 gram Bloom with the proviso that said block copolymers without amorphous midblocks are combined with at least one block copolymer having at least one amorphous midblock, wherein said block midblocks of copolymers forming said crystal gel having a selected amount of crystallinity sufficient to exhibit a melting endotherm of at least about 40° C. as determined by DSC curve.

2. An improved gelatinous composition comprising: a crystal gel formed from 100 parts by weight of one or more block copolymers or mixtures of two or more such block copolymers, said block copolymers having the formula poly(styrene-ethylene-ethylene-butylene-styrene), poly(styrene-ethyleneb$_{45}$-ethylene-propylene-styrene), poly(styrene-ethylene-ethylene-butylene$_{25}$-styrene), poly(styrene-ethylene-ethylene-propylene-ethylene-s), poly(styrene-ethylene-propylene-ethylene-styrene), poly(styrene-ethylene-propylene-ethylene-ethylene-propylene-styrene), poly(styrene-ethylene-ethylene-butylene)$_n$, poly(styrene-ethyleneb$_{45}$-ethylene-propylene)$_n$, poly(styrene-ethylene ethylene-butylene$_{25}$)$_n$, poly(styrene-ethylene-ethylene-propylene-ethylene)$_n$, poly(styrene-ethylene-propylene-ethylene)$_n$, poly(styrene-ethylene-propylene-ethylene-ethylene)$_n$, midblocks comprising one or more substantially crystalline polyethylene midblock segment, wherein subscript n is two or more in combination with or without a selected amount of one or more of a (II) polymer or copolymer, and selected amounts of a plasticizing oil (III) sufficient to achieve gel rigidities of from less than about 2 gram Bloom to about 1,800 gram Bloom, said gel having greater tear resistance or greater fatigue resistance than amorphous poly(styrene-ethylene-butylene-styrene) or poly(styrene-ethylene-propylene-styrene) gels.

3. A gel according to claim 1 or 2, wherein said midblock copolymer segment having a crystallinity of at least about 20 mole % of (—CH$_2$—)16 units forming said midblock of the block copolymer.

4. A gel according to claim 1 or 2, wherein said gel exhibits in differential scanning calorimeter (DCS) a melting endotherm of about 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 90° C., 100° C., 110° C., or 120° C.

5. A. A gel according to claim 1 or 2, wherein said (I) block copolymer is formed in combination with a selected amount of one or more selected polymer or copolymer selected from the group consisting of poly(styrene-butadiene-styrene), poly(styrene-butadiene), poly(styrene-isoprene-styrene), poly(styrene-isoprene), poly(styrene-ethylene-propylene), poly(styrene-ethylene-propylene-styrene), poly(styrene-ethylene-butylene-styrene), poly(styrene-ethylene-butylene), poly(styrene-ethylene-propylene)n, poly(styrene-ethylene-butylene)n, maleated poly(styrene-ethylene-propylene-styrene), maleated poly(styrene-ethylene-butylene-styrene), maleated poly(styrene-ethylene-butylene), maleated poly(styrene-ethylene-propylene)n, maleated poly(styrene-ethylene-butylene)n, polystyrene, polybutylene, poly(ethylene-propylene), poly(ethylene-butylene), polypropylene, polyethylene, polyethyleneoxide, poly(dimethylphenylene oxide), copolymers of trifluoromethyl-4,5-difuoro-1,3-dioxole and tetrafluoroethylene, tetrafluoroethylene, polycarbonate, ethylene vinyl alcohol copolymer, polyamide or polydimethylsiloxane; wherein said selected copolymer is a linear, branched, radial, or multiarm copolymer.

6. A gel according to claim 1 or 2, wherein said gel is being denoted by G, is physically interlocked with a selected material M forming a composite of the combination G$_n$M$_n$, G$_n$M$_n$G$_n$, M$_n$G$_n$M$_n$, M$_n$G$_n$G$_n$M$_n$, G$_n$M$_n$M$_n$G$_n$, G$_n$M$_n$G$_n$M$_n$G$_n$, M$_n$M$_n$M$_n$G$_n$, M$_n$M$_n$M$_n$G$_n$M$_n$M$_n$M$_n$ or a permutation of one or more of said G$_n$ with M$_n$; wherein when n is a subscript of M, n is the same or different selected from the group consisting of paper, foam, plastic, fabric, metal, metal foil, concrete, wood, glass, glass fibers, ceramics, synthetic resin, synthetic fibers or refractory materials; and wherein when n is a subscript of G, n denotes the same or a different gel rigidity.

7. A gel according to claim 1 or 2, wherein said gel being formed into a gel hand exercising grip, a gel shape floss suitable for use as a dental floss, a gel crutch cushion, a gel cervical pillow, a gel bed wedge pillow, a gel leg rest, a gel neck cushion, a gel mattress, a gel bed pad, a gel elbow pad, a gel dermal pad, a gel wheelchair cushion, a gel helmet liner, a gel cold and hot pack, a gel exercise weight belt, a gel traction pad or belt, a gel cushion for splints, a gel sling, a gel brace for the hand, wrist, finger, forearm, knee, leg, clavicle, shoulder, foot, ankle, neck, back, rib, a gel sole for orthopedic shoe, a gel shaped toy article, a gel optical cladding for cushioning optical fibers from bending stresses, a gel swab tip, a gel fishing bate, a gel seal against pressure, a gel thread, a gel strip, a gel yarn, a gel tape, a weaved gel cloth, a gel fabrics, a gel balloon for valvuloplasty of the mitral valve, a gel trointestinal balloon dilator, a gel esophageal balloon dilator, a gel dilating balloon catheter use in coronary angiogram, a gel condom, a gel toy balloon, a gel surgical and examination glove, a self sealing enclosures for splicing electrical and telephone cables and wires, a gel film, or a gel liner.

8. A gel according to claim 1 or 2, wherein said gel is being denoted by G, is physically interlocked with a selected material M forming a composite of the combination G$_n$G$_n$, G$_n$G$_n$G$_n$, M$_n$G$_n$G$_n$, M$_n$M$_n$M$_n$G$_n$M$_n$, G$_n$M$_n$G$_n$G$_n$, G$_n$GM$_n$M$_n$, G$_n$G$_n$M$_n$ G$_n$M$_n$G$_n$G$_n$, G$_n$M$_n$G$_n$, M$_n$G$_n$M$_n$G$_n$M$_n$G$_n$, G$_n$G$_n$M$_n$M$_n$G$_n$, G$_n$G$_n$M$_n$G$_n$M$_n$G$_n$ or a permutation of one or more of said G$_n$ with M$_n$; wherein when n is a subscript of M, n is the same or different selected from the group consisting of paper, foam, plastic, fabric, metal, metal foil, concrete, wood, glass, glass fibers, ceramics, synthetic resin, synthetic fibers or refractory materials; and wherein when n is a subscript of G, n denotes the same or a different gel rigidity.

9. A composite of claim 6 shaped in the form of a gel liner for lower limb or above the knee amputee prosthesis formed by injection molding, extruding, spinning, casting, or dipping of said gel in combination with M selected from foam, plastic, fabric, metal, ceramics, synthetic resin, synthetic fibers or refractory materials.

10. A composite of claim 8 shaped in the form of a gel liner for lower limb above the knee amputee prosthesis formed by injection molding, extruding, spinning, casting, or dipping of said gel in combination with or without M selected from foam, plastic, fabric, metal, ceramics, synthetic resin, synthetic fibers, or refractory materials and in combination with or without one or more gels having a different rigidity.

* * * * *

UNITED STATES PATENT AND TRADEMARK OFFICE
CERTIFICATE OF CORRECTION

PATENT NO.    : 6,117,176
DATED         : September 12, 2000
INVENTOR(S)   : John Y. Chen It is certified that error appears in the above-identified patent and that said Letters Patent is hereby corrected as shown below:

Column 1,
Line 14, after year "1994" delete ";".
Line 14, after the number "286" add -- ; --.
Lines 21-25, delete the following:
"which in turn is a CIP of 957,290); now U.S. Pat. No. 5,334,646 Ser. No. 08/152,743, filed Nov. 15, 1993 now U. S. Pat. No. 5,629.294 (CIPs of 114.688; 935,540; 876,118; 705,096; 957,290; 705,711"
and add
-- The above patents and applications are specifically incorporated herein by reference. --.

Figure 3A:
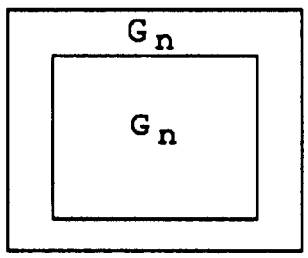
FIGS. 3a–3n. Representative sectional view of composite articles.
Figure 3B:
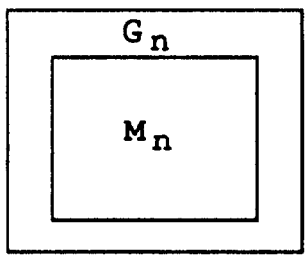
Figure 3C:
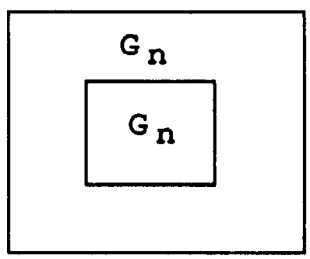
Figure 3D:
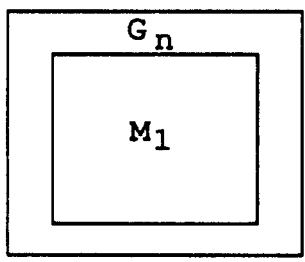
Figure 3E:
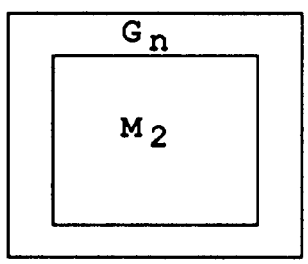
Figure 3F:
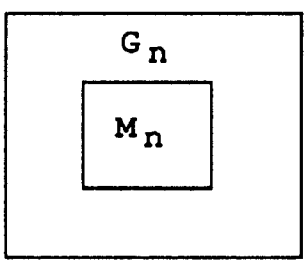
Figure 3G:
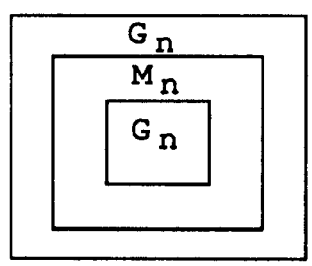
Figure 3H:
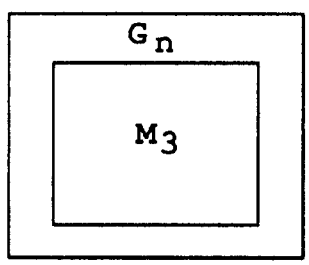
Figure 3I:
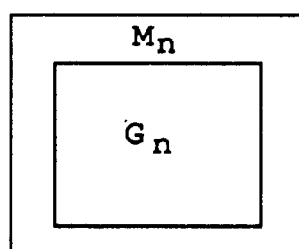
Figure 3J:
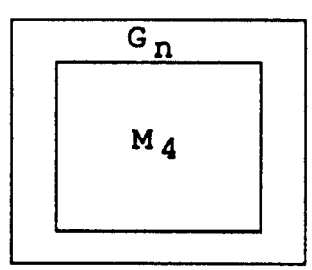
Figure 3K:
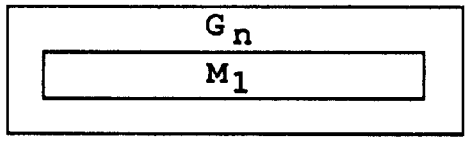
Figure 3L:
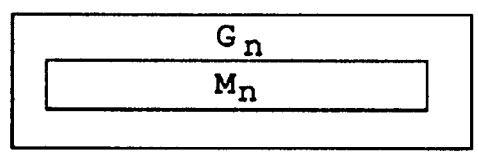
Figure 3M:
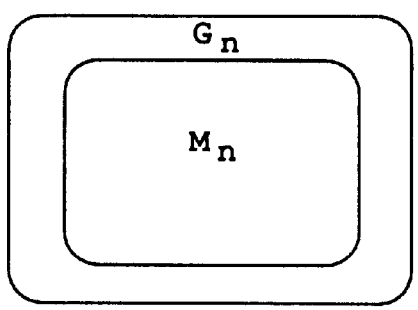
Figure 3N:
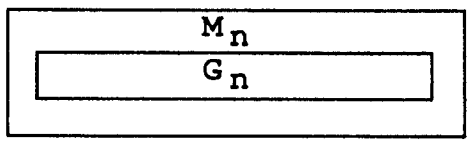

Column 3,
Line 23, after the word "articles" before the period add the following:

-- as shown generally by the relationship of $G_n$ and $M_n$ and more specific article examples of $M_1$, $M_2$, $M_3$, and $M_4$ with $G_n$ when the material $M_n$ is n = 1 (fabric/cloth), n = 2 (foam/sponge), n = 3 (synthetic resin/plastic), and n = 4 (fibre) a s shown in Figs 3d, 3e, 3h, and 3j respectively --.

Figure 4A:
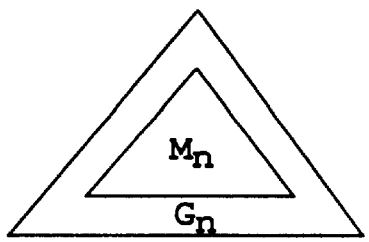
FIGS. 4a–4w. Representative sectional view of composite articles.
Figure 4B:
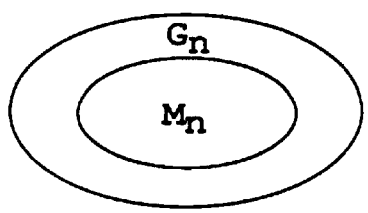
Figure 4C:
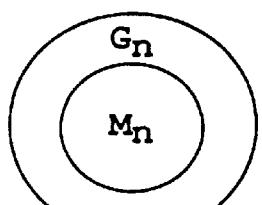
Figure 4D:
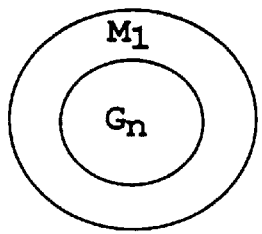
Figure 4E:
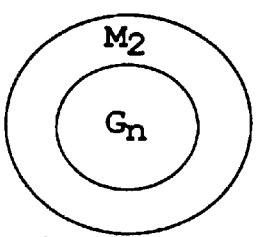
Figure 4F:
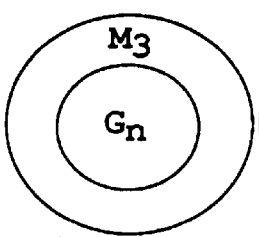
Figure 4G:
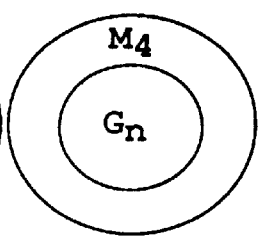
Figure 4H:
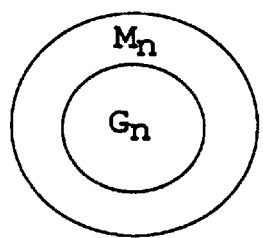
Figure 4I:
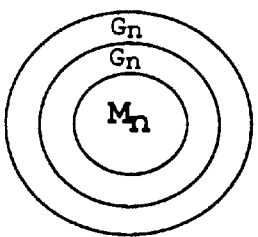
Figure 4J:
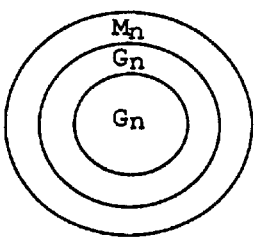
Figure 4K:
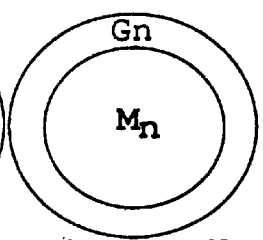
Figure 4L:
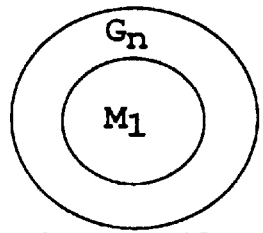
Figure 4M:
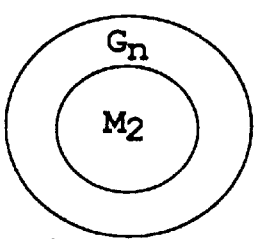
Figure 4N:
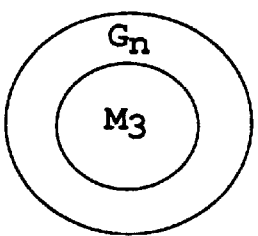
Figure 4O:
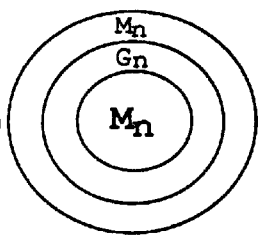
Figure 4P:
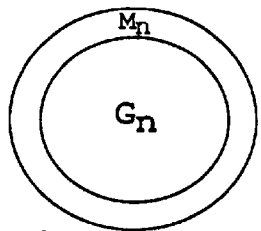
Figure 4Q:
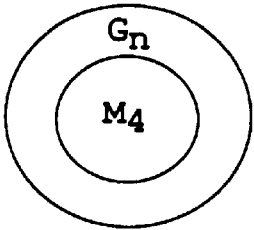
Figure 4R:
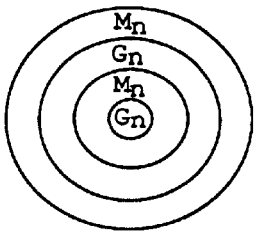
Figure 4S:
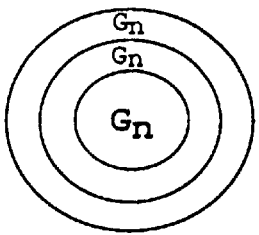
Figure 4T:
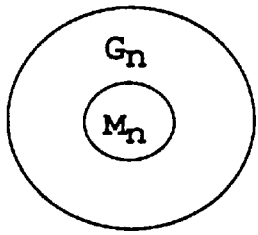
Figure 4U:
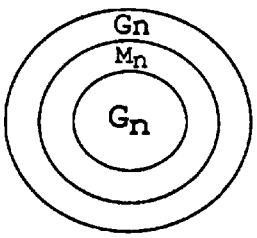
Figure 4V:
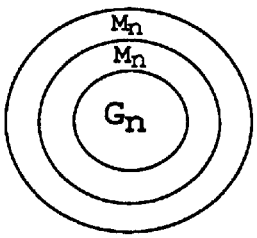
Figure 4W:
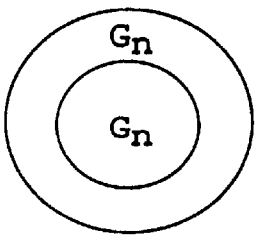

Line 25, after the word "articles" before the period add the following:

-- as shown generally by the relationship of $G_n$ and $M_n$ and more specific article examples of $M_1$, $M_2$, $M_3$, and $M_4$ with $G_n$ when the material $M_n$ is n = 1 (fabric/cloth), n = 2 (foam/sponge), n = 3 (synthetic resin/plastic), and n = 4 (fibre) a s shown in Figs 4l, 4m, 4n, and 4q respectively --.

Line 26, delete the polymer notation: "S-E-EB-S" and add -- S-E-EP-S --.

Column 6,
Line 59, "poly(butadine)" and add -- poly(butadiene) --.

Column 9,
Line 8, delete "polybutadine" and add -- polybutadiene --.
Line 54, delete "negligable" and add -- negligible --.
Line 67, delete "detactable" and add -- detectable --.

Column 10,
Line 47, delete "resutls" and add -- results --.

Column 12,
Line 15, delete "glass a transition" and add -- a glass transition --.

UNITED STATES PATENT AND TRADEMARK OFFICE
CERTIFICATE OF CORRECTION

PATENT NO.   : 6,117,176
DATED        : September 12, 2000
INVENTOR(S)  : John Y. Chen It is certified that error appears in the above-identified patent and that said Letters Patent is hereby corrected as shown below:

Column 13,
Line 9, delete "amorpous" and add -- amorphous --.

Column 15,
Line 44, delete "steraric" and add -- stearic --.

Column 23,
Lines 2-20, correct claim 1 by deleting:

"1. An improved gelatinous composition comprising: a crystal gel formed from (I) 100 parts by weight of one or more linear, branched, star-shaped (radial), or multiarm block copolymers or mixtures of two or more such block copolymers, said block copolymers having one or more midblocks, said midblocks comprising one or more substantially crystalline polyethylene midblocks and with one or more amorphous midblocks; optionally in combination with a selected amount of one or more of (II) a polymer or copolymer, and selected amounts of a plasticizing oil (III) sufficient to achieve gel rigidities of from less than about 2 gram Bloom to about 1,800 gram Bloom with the proviso that said block copolymers without any amorphous midblocks are combined with at least one block copolymer having at least one amorphous midblock, wherein said block midblocks of copolymers forming said crystal gel having a selected amount of crystallinity sufficient to exhibit a melting endotherm of at least about 40°C as determined by DSC curve."

and adding the corrected claim 1 as follows:

-- 1. An improved gelatinous composition comprising: a crystal gel formed from (I) 100 parts by weight of one or more linear, branched, star-shaped (radial), or multiarm block copolymers or mixtures of two or more such block copolymers, said block copolymers having one or more midblocks, said midblocks comprising one or more substantially crystalline polyethylene midblocks and with (I) one or more amorphous midblocks or (ii) without amorphous midblocks, in combination with or without a selected amount of one or more of (II) a polymer or copolymer, and selected amounts of (III) a plasticizing oil sufficient to achieve gel rigidities of from less than about 2 gram Bloom to about 1,800 gram Bloom, with the proviso when said (I) block copolymers without any amorphous midblocks are combined with at least one block copolymer having at least one amorphous midblock, that said midblocks of said (I) block copolymers forming said crystal gel comprises a selected amount of crystallinity sufficient to exhibit a melting endotherm of at least about 40°C as determined by DSC curve. --

UNITED STATES PATENT AND TRADEMARK OFFICE
CERTIFICATE OF CORRECTION

PATENT NO. : 6,117,176
DATED : September 12, 2000
INVENTOR(S) : John Y. Chen

It is certified that error appears in the above-identified patent and that said Letters Patent is hereby corrected as shown below:

<u>Column 23 cont'd,</u>
Lines 21-45, correct claim 2 by deleting:

"2. An improved gelatinous composition comprising: a crystal gel formed from 100 parts by weight of one or more block copolymers or mixtures of two or more such block copolymers, said block copolymers having the formula poly(styrene-ethylene-ethylene-butylene-styrene), poly(styrene-ethyleneb$_{45}$-ethylene-propylene-styrene), poly(styrene-ethylene-ethylene-butylene$_{25}$-styrene), poly(styrene-ethylene-ethylene-propylene-styrene), poly(styrene-ethylene-propylene-ethylene-styrene), poly(styrene-ethylene-propylene-ethylene-ethylene-propylene-styrene),poly(styrene-ethylene-ethylene-butylene)$_n$, poly(styrene-ethyleneb$_{45}$-ethylene-propylene)$_n$, poly(styrene-ethylene-ethylene-butylene$_{25}$)$_n$, poly(styrene-ethylene-ethylene-propylene-ethylene)$_n$, poly(styrene-ethylene-propylene-ethylene)$_n$, poly(styrene-ethylene-propylene-ethylene-ethylene)$_n$, midblocks comprising one or more substantially crystalline polyethylene midblock segment, wherein subscript n is two or more; in combination with or without a selected amount of one or more of a (II) polymer or copolymer, and selected amounts of a plasticizing oil (III) sufficient to achieve gel rigidities of from less than about 2 gram Bloom to about 1,800 gram Bloom, wherein said gel is capable of exhibiting greater tear resistance or greater fatigue resistance than a gel having a corresponding rigidity made from a substantially amorphous poly(styrene-ethylene-butylene-styrene) or poly(styrene-ethylene-propylene-styrene) block copolymers having substantially non-crystalline polyethylene midblock segments."

add the corrected claim 2 as follows:

-- 2. An improved gelatinous composition comprising: a crystal gel formed from (I) 100 parts by weight of one or more of the same block copolymers or mixtures of two or more of a different block copolymers, said block copolymers having the formula poly(styrene-ethylene-ethylene-butylene-styrene), poly(styrene-ethylene-ethylene-propylene-styrene), poly(styrene-ethylene-ethylene-butylene$_{25}$-styrene), poly(styrene-ethylene-ethylene-propylene-ethylene-styrene), poly(styrene-ethylene-propylene-ethylene-styrene), poly(styrene-ethylene-propylene-ethylene-ethylene-propylene-styrene), poly(styrene-ethylene-ethylene-butylene)$_n$, poly(styrene-ethylene-ethylene-propylene)$_n$, poly(styrene-ethylene-ethylene-butylene$_{25}$)$_n$, poly(styrene-ethylene-ethylene-propylene-ethylene)$_n$, poly(styrene-ethylene-propylene-ethylene)n, poly(styrene-ethylene-propylene-ethylene-ethylene-propylene)$_n$, midblocks comprising one or more substantially crystalline polyethylene midblock segment(s), wherein subscript n is two or more; wherein said (I) block copolymers in combination with or without a selected amount of one or more of (II) a polymer or copolymer, and selected amounts of (III) a plasticizing oil sufficient to achieve a gel rigidity of from less than about 2 gram Bloom to about 1,800 gram Bloom, wherein said gel is capable of exhibiting greater tear resistance or greater fatigue resistance than a gel having a corresponding rigidity made from a substantially amorphous poly(styrene-ethylene-butylene-styrene) or poly(styrene-ethylene-propylene-styrene) block copolymers having substantially non-crystalline polyethylene midblock segments. --

UNITED STATES PATENT AND TRADEMARK OFFICE
CERTIFICATE OF CORRECTION

PATENT NO. : 6,117,176
DATED : September 12, 2000
INVENTOR(S) : John Y. Chen

It is certified that error appears in the above-identified patent and that said Letters Patent is hereby corrected as shown below:

Column 23 cont'd,
Lines 50-59, correct claim 4 by deleting:

"4. (Once amended) A gel according to claim 1 or 2, wherein said gel exhibits in differential scanning calorimeter (DCS) a melting endotherm of about 28°C, 29°C, 30°C, 31°C, 32°C, 33°C, 34°C, 35°C, 36°C, 37°C, 38°C, 39°C, 40°C, 41°C, 42°C, 43°C, 44°C, 45°C, 46°C, 47°C, 48°C, 49°C, 50°C, 51°C, 52°C, 53°C, 54°C, 55°C, 56°C, 57°C, 58°C, 59°C, 60°C, 61°C, 62°C, 63°C, 64°C, 65°C, 66°C, 67°C, 68°C, 69°C, 70°C, 71°C, 72°C, 73°C, 74°C, 75°C, 76°C, 77°C, 78°C, 79°C, 80°C, 90°C, 100°C, 110°C, or 120°C."

add the corrected claim 4 as follows:

4. A gel according to claim 1 or 2, wherein said gel exhibits in differential scanning calorimeter (DSC) a melting endotherm of about 25°C, 28°C, 29°C, 30°C, 31°C, 32°C, 33°C, 34°C, 35°C, 36°C, 37°C, 38°C, 39°C, 40°C, 41°C, 42°C, 43°C, 44°C, 45°C, 46°C, 47°C, 48°C, 49°C, 50°C, 51°C, 52°C, 53°C, 54°C, 55°C, 56°C, 57°C, 58°C, 59°C, 60°C, 61°C, 62°C, 63°C, 64°C, 65°C, 66°C, 67°C, 68°C, 69°C, 70°C, 71°C, 72°C, 73°C, 74°C, 75°C, 76°C, 77°C, 78°C, 79°C, 80°C, 90°C, 100°C, 110°C, or 120°C. --

Column 24,
Lines 14-25, correct claim 6 by deleting:

"6. A gel according to claim 1 or 2, wherein said gel is being denoted by G, is physically interlocked with a selected material M forming a composite of the combination $G_nM_n$, $G_nM_nG_n$, $M_nG_nM_n$, $M_nG_nG_nM_n$, $G_nM_nM_nG_n$, $G_nM_nG_nM_nG_n$, $M_nM_nM_nG_n$, $M_nM_nM_nG_nM_nM_nM_n$ or a permutation of one or more of said $G_n$ with $M_n$; wherein when n is a subscript of M, n is the same or different selected from the group consisting of paper, foam, plastic, fabric, metal, metal foil, concrete, wood, glass, glass fibers, ceramics, synthetic resin, synthetic fibers or refractory materials; and wherein when n is a subscript of G, n denotes the same or a different gel rigidity."

add correced claim 6 as follows:

-- 6. A gel according to claim 1 or 2, wherein said gel is being denoted by G, is physically interlocked with a selected material M or in combination with one or more of the same gel or a different gel forming a composite of the combination $G_nG_n$, $G_nG_nG_n$, $G_nM_n$, $G_nM_nG_n$, $M_nG_nM_n$, $M_nG_nG_n$, $M_nM_nM_nG_nM_n$, $M_nG_nG_nM_n$, $G_nM_nG_nG_n$, $G_nG_nM_nM_n$, $G_nM_nM_nG_n$, $G_nG_nM_nG_nM_nG_nG_n$, $G_nM_nG_nM_nM_n$, $M_nG_nM_nG_nM_nG_n$, $G_nG_nM_nM_nG_n$, $G_nG_nM_nG_nM_n$, $G_nG_nM_nG_nM_nG_n$, $G_nM_nG_nM_nG_n$, $M_nM_nM_nG_n$, $M_nM_nM_nG_nM_nM_nM_n$ or a permutation of one or more of said $G_n$ with $M_n$; wherein when n is a subscript of M, n is the same or different selected from the group consisting of paper, foam, plastic, fabric, metal, metal foil, concrete, wood, glass, glass fibers, ceramics, synthetic resin, synthetic fibers or refractory materials; and wherein when n is a subscript of G, n denotes the same or a different gel rigidity.--

UNITED STATES PATENT AND TRADEMARK OFFICE
CERTIFICATE OF CORRECTION

PATENT NO. : 6,117,176
DATED : September 12, 2000
INVENTOR(S) : John Y. Chen

It is certified that error appears in the above-identified patent and that said Letters Patent is hereby corrected as shown below:

Column 24 cont'd,
Lines 26-46, correct claim 7 by deleting:

"7. (Twice amended) A gel according to claim 1 or 2 wherein said gel being formed into a gel hand exercising grip, a gel shape floss suitable for use as a dental floss, a gel crutch cushion, a gel cervical pillow, a gel bed wedge pillow, a gel leg rest, a gel neck cushion, a gel mattress, a gel bed pad, a gel elbow pad, a gel dermal pad, a gel wheelchair cushion, a gel helmet liner, a gel cold and hot pack, a gel exercise weight belt, a gel traction pad or belt, a gel cushion for splints, a gel sling, a gel brace for the hand, wrist, finger, forearm, knee, leg, clavicle, shoulder, foot, ankle, neck, back, rib, a gel sole for orthopedic shoe, a gel shaped toy article, a gel optical cladding for cushioning optical fibers from bending stresses, a gel swab tip, a gel fishing bate, a gel seal against pressure, a gel thread, a gel strip, a gel yarn, a gel tape, a weaved gel cloth, a gel fabrics, a gel balloon for valvuloplasty of the mitral valve, a gel trointestinal balloon dilator, a gel esophageal balloon dilator, a gel dilating balloon catheter use in coronary angiogram, a gel condom, a gel toy balloon, a gel surgical and examination glove, a self sealing enclosures for splicing electrical and telephone cables and wires, a gel film, or a gel liner."

add the corrected claim 7 as follows:

-- 7. A gel according to claim 1 or 2, wherein said gel being formed into a gel hand exercising grip, a gel shape floss suitable for use as a dental floss, a gel crutch cushion, a gel cervical pillow, a gel bed wedge pillow, a gel leg rest, a gel neck cushion, a gel mattress, a gel bed pad, a gel elbow pad, a gel dermal pad, a gel wheelchair cushion, a gel helmet liner, a gel cold and hot pack, a gel exercise weight belt, a gel traction pad or belt, a gel cushion for splints, a gel sling, a gel brace for the hand, wrist, finger, forearm, knee, leg, clavicle, shoulder, foot, ankle, neck, back, rib, a gel sole for orthopedic shoe, a gel shaped toy article, a gel optical cladding for cushioning optical fibers from bending stresses, a gel swab tip, a gel fishing bate, a gel seal against pressure, a gel thread, a gel strip, a gel yarn, a gel tape, a weaved gel cloth, a gel fabrics, a gel balloon for valvuloplasty of the mitral valve, a gel trointestinal balloon dilator, a gel esophageal balloon dilator, a gel dilating balloon catheter use in coronary angiogram, a gel condom, a gel toy balloon, a gel surgical and examination glove, a self sealing enclosures for splicing electrical and telephone cables and wires, a gel film, or a gel liner. --

Lines 47-59, correct claim 8 by deleting:

"8. A gel according to claim 1 or 2, wherein said gel is being denoted by G, is physically interlocked with a selected material M or in combination with one or more of the same gel or different gel forming a composite of the combination $G_nG_n$, $G_nG_nG_n$, $G_nM_n$, $G_nM_nG_n$, $M_nG_nM_n$, $M_nG_nG_n$, $M_nM_nM_nG_nM_n$, $M_nG_nG_nM_n$, $G_nM_nG_nG_n$, $G_nG_nM_nM_n$, $G_nM_nM_nG_n$, $G_nG_nM_nG_nM_nG_nG_n$, $G_nM_nG_nM_nM_n$, $M_nG_nM_nG_nM_nG_n$, $G_nG_nM_nM_nG_n$, $G_nG_nM_nG_nM_n$, $G_nG_nM_nG_nM_nG_n$ or a permutation of one or more of said $G_n$ with $M_n$; wherein when n is a subscript of M, n is the same or different selected from the group consisting of paper, foam, plastic, fabric, metal, metal foil, concrete, wood, glass, glass fibers, ceramics, synthetic resin, synthetic fibers or refractory materials; and wherein when n is a subscript of G, n denotes the same or a different gel rigidity."

UNITED STATES PATENT AND TRADEMARK OFFICE
CERTIFICATE OF CORRECTION

PATENT NO. : 6,117,176
DATED : September 12, 2000
INVENTOR(S) : John Y. Chen

It is certified that error appears in the above-identified patent and that said Letters Patent is hereby corrected as shown below:

Column 24 cont'd,
Add the corrected claim 8 as follows:

-- 8. A gel according to claim 5, wherein said composite being formed into a gel hand exercising grip, a gel shape floss suitable for use as a dental floss, a gel crutch cushion, a gel cervical pillow, a gel bed wedge pillow, a gel leg rest, a gel neck cushion, a gel mattress, a gel bed pad, a gel elbow pad, a gel dermal pad, a gel wheelchair cushion, a gel helmet liner, a gel cold and hot pack, a gel exercise weight belt, a gel traction pad or belt, a gel cushion for splints, a gel sling, a gel brace for the hand, wrist, finger, forearm, knee, leg, clavicle, shoulder, foot, ankle, neck, back, rib, a gel sole for orthopedic shoe, a gel shaped toy article, a gel optical cladding for cushioning optical fibers from bending stresses, a gel swab tip, a gel fishing bate, a gel seal against pressure, a gel thread, a gel strip, a gel yarn, a gel tape, a weaved gel cloth, a gel fabrics, a gel balloon for valvuloplasty of the mitral valve, a gel trointestinal balloon dilator, a gel esophageal balloon dilator, a gel dilating balloon catheter use in coronary angiogram, a gel condom, a gel toy balloon, a gel surgical and examination glove, a self sealing enclosures for splicing electrical and telephone cables and wires, a gel film, or a gel liner. --

Lines 60-65, correct claim 9 by deleting:

"9. A composite of claim 6 shaped in the form of a gel liner for lower limb or above the knee amputee prosthesis formed by injection molding, extruding, spinning, casting, or dipping of said gel in combination with M selected from foam, plastic, fabric, metal, ceramics, synthetic resin, synthetic fibers or refactory materials."

add the corrected claim 9 as follows:

-- 9. A composite of claim 6 shaped in the form of a gel liner for lower limb or above the knee amputee prosthesis formed by injection molding, extruding, spinning, casting, or dipping of said gel, wherein said gel comprises at least one said block copolymer of poly(styrene-ethylene-ethylene-propylene-styrene), poly(styrene-ethylene-ethylene-propylene)$_n$, poly(styrene-ethylene-ethylene-butylene-styrene), or poly(styrene-ethylene-ethylene-butylene)$_n$ or a mixture of two or more of said block copolymers. --

UNITED STATES PATENT AND TRADEMARK OFFICE
CERTIFICATE OF CORRECTION

PATENT NO. : 6,117,176
DATED : September 12, 2000
INVENTOR(S) : John Y. Chen

It is certified that error appears in the above-identified patent and that said Letters Patent is hereby corrected as shown below:

Columns 24, 25 & 26,
Lines 66-67, 1-4 & 1-2, correct claim 10 respectively by deleting:

"10. A composite of claim 8 shaped in the form of a gel liner for lower limb or above the knee amputee prosthesis formed by injection molding, extruding, spinning, casting, or dipping of said gel in combination with or without M selected from foam, plastic, fabric, metal, ceramics, synthetic resin, synthetic fibers or refactory materials and in combination with or without one or more gels having a different rigidity."

add the corrected claim 10 as follows:

-- 10. A gel of claim 4 shaped in the form of a gel liner for lower limb or above the knee amputee prosthesis formed by injection molding, extruding, spinning, casting, or dipping of said gel, wherein said gel comprises at least one said block copolymer of poly(styrene-ethylene-ethylene-propylene-styrene), poly(styrene-ethylene-ethylene-propylene)$_n$, poly(styrene-ethylene-ethylene-butylene-styrene), or poly(styrene-ethylene-ethylene-butylene)$_n$, or a mixture of two or more of said block copolymers. --

Signed and Sealed this

Twenty-eighth Day of October, 2003

JAMES E. ROGAN
*Director of the United States Patent and Trademark Office*